United States Patent
Moon et al.

(10) Patent No.: US 7,361,719 B2
(45) Date of Patent: Apr. 22, 2008

(54) MONOMER WITH ANTI-MICROBIAL CHARACTER, POLYMER USING THE SAME, AND MANUFACTURING METHOD THEREOF

(75) Inventors: Woong-Sig Moon, Suwon (KR); Jae-Chul Kim, Suwon (KR); Kyoo-Hyun Chung, Seou (KR); Ki-Oh Kong, Incheon (KR); Jung-Hwa Hwang, Seoul (KR)

(73) Assignee: Micro Science Tech Co., Ltd., Hwaseong (KR)

( * ) Notice: Subject to any disclaimer, the term of this patent is extended or adjusted under 35 U.S.C. 154(b) by 377 days.

(21) Appl. No.: 10/503,040

(22) PCT Filed: Feb. 3, 2003

(86) PCT No.: PCT/KR03/00238

§ 371 (c)(1),
(2), (4) Date: Apr. 15, 2005

(87) PCT Pub. No.: WO03/064412

PCT Pub. Date: Aug. 7, 2003

(65) Prior Publication Data

US 2005/0176905 A1   Aug. 11, 2005

(30) Foreign Application Priority Data

Jan. 31, 2002 (KR) ............... 10-2002-0005728
Jun. 25, 2002 (KR) ............... 10-2002-0035792
Feb. 3, 2003 (KR) ............... 10-2003-0006509

(51) Int. Cl.
*C08F 20/26* (2006.01)
*C08F 26/06* (2006.01)

(52) U.S. Cl. .............. 526/320; 526/242; 526/258; 526/265; 526/307.5; 526/307.6; 526/307.7; 526/318; 526/318.4; 526/338; 526/342; 526/347

(58) Field of Classification Search ........... 526/242, 526/258, 265, 307.5, 307.6, 307.7, 318, 318.4, 526/320, 338, 342, 347
See application file for complete search history.

(56) References Cited

U.S. PATENT DOCUMENTS 5,969,141 A   10/1999   Petersen et al.

FOREIGN PATENT DOCUMENTS

JP   03-209367   9/1991

OTHER PUBLICATIONS

H. Kondo, F. Sakamoto, Y. Inoue and G. Tsukamoto; *Studies on product. 10. Possible mechanism of N-dealkylation of N-masked norfloxacins having several active methylene groups*; J. Med. Chem.; Mar. 1989; vol. 32, No. 3; pp. 679-682; Pharmaceuticals Research Center, Kaneobo, Ltd., Osaka, Japan.
G.L. Woo, M.W. Mittelman and J.P. Santerre; *Synthesis and characterization of a novel biodegradable antimicrobial polymer*; Biomaterials; Jun. 2000; vol. 21, No. 12; pp. 1235-1246; Department of Chemical Engineering and Applied Chemistry, Faculty of Engineering, University of Toronto, Ontario, Canada.
Copy of International Search Report for PCT/KR03/00238 completed Jun. 10, 2003.

*Primary Examiner*—Helen L Pezzuto
(74) *Attorney, Agent, or Firm*—Alston & Bird LLP

(57) ABSTRACT

The present invention relates to a monomer with antimicrobial characteristics, a polymeric compound with antimicrobial characteristics using the same, and manufacturing methods thereof, and more particularly, to an antimicrobial monomer comprising a saturated hydrocarbon having a polymerizable functional group within its structure. Also, the present invention provides a polymeric compound using the above antimicrobial monomer, a manufacturing method thereof, and a polymeric resin composition. The compounds according to the present invention have durable antimicrobial activity and high heat resistance, they do not give rise to toxicity when added to conventional resins by not eluting the antimicrobial compounds, and they do not have an effect on the properties of molded products.

3 Claims, No Drawings

MONOMER WITH ANTI-MICROBIAL CHARACTER, POLYMER USING THE SAME, AND MANUFACTURING METHOD THEREOF

BACKGROUND OF THE INVENTION (a) Field of the Invention

The present invention relates to a monomer with antimicrobial characteristics, a polymeric compound with antimicrobial characteristics using the same, and manufacturing methods thereof, and more particularly, to an antimicrobial monomer that has durable antimicrobial activity and high heat resistance, does not give rise to toxicity when added to conventional polymeric resins and petrochemical products by not eluting antimicrobial compounds, and does not have an effect on the properties of molded products, an antimicrobial polymer using the same, and manufacturing methods thereof.

(b) Description of the Related Art

Recently, in line with great concerns about environmental hygiene and high-grade life style, the production of and demand for products conferring antimicrobial characteristics to petrochemical materials for use in industrial supplies such as food wrappers, containers for storage, toothbrushes, cutting boards, stationery, washing tubs, water purifiers, shampoos, soaps, cosmetics and wrappers, and medical supplies, are increasing.

In the case of organic antimicrobial substances used in these products (ex: quaternary ammonium salts, triazines, benzimidazole, triclosan, chlorohexidine, thiazoles, etc.), in order to confer antimicrobial ability to polymeric substances, the antimicrobial substances are simply added to the polymeric substances when manufacturing antimicrobial materials. However, it has been reported that the antimicrobial materials have technical limits in respect to the inherent toxicity of antimicrobial substances, the elution of antimicrobial substances, the reduction of antimicrobial ability due to the elution, and so on. Especially in the case of injecting or extruding plastics, antimicrobial substances may be decomposed by high heat, and they may also induce a yellowing phenomenon (low heat resistance).

In order to overcome the limits as described above, a simple mixing method with inorganic ceramic anti-microbial complexes is widely used. However, such a method also has the problem that the antimicrobial activities are chemically decreased when they come into contact with moisture (JAPAN NEWS Feb. 11 (Wed.), 1998, Monthly Ceramics No. 2, 1998). In addition, research on binding antimicrobial substances to polymers is in progress. Pittman disclosed a method of co-polymerizing pentachlorophenylacrylates and acrylic monomers in 1981 (Pittman et al., J. Appl. Polym. Sci., 1981, 26, 2403), and Korean Patent Application No. 97-62102 disclosed a method of directly mixing antimicrobial agents with fibers, leathers, or plastics, and molding and processing them using the chemical reaction between the antimicrobial agents and polymers. However, such methods still did not solve the problems of quality deterioration of products since the antimicrobial ability was lost due to heat degradation during manufacturing processes, yellowing occurred, and the mechanical properties of the molded articles deteriorated or dispersion in the formed articles was poor. Moreover, U.S. Pat. No. 5,798,115 disclosed a method of using quinolinecarboxylic compounds as a back bone, but it also did not solve the problems owing to the elution of antimicrobial substances.

SUMMARY OF THE INVENTION

Therefore, the present invention has been made to solve the problems of the prior arts as described, and it is an object of the invention to provide an antimicrobial monomer having durable antimicrobial activity with excellent heat resistance and compatibility.

It is another object of the present invention to provide a method of manufacturing a novel antimicrobial monomer compound.

It is a still another object of the invention to provide an antimicrobial polymeric compound having durable antimicrobial activity with excellent heat resistance and compatibility using the above antimicrobial monomer compound and a manufacturing method thereof.

It is still another object of the invention is to provide a polymeric resin composition comprising the above antimicrobial monomer or the antimicrobial polymeric compound using it.

It is still another object of the invention is to provide a method of applying the antimicrobial monomer compound as a coating agent for UV light by simply adding it to petrochemical products and chemically irradiating it with UV light (by virtue of the presence of reactive groups).

In order to achieve the aforementioned objects, the present invention provides an antimicrobial monomer compound represented by the following formula 1:

[Formula 1]

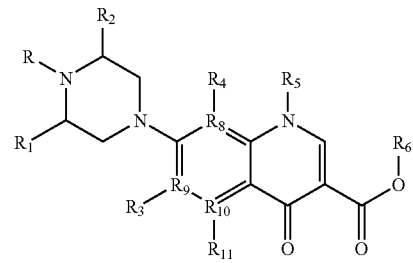

wherein

R is a saturated or unsaturated $C_1$ to $C_{150}$ hydrocarbon comprising a polymerizable functional group and a light-curable reactive functional group;

$R_1$ and $R_2$ are each independently or simultaneously hydrogen, a halogen atom, an amine, or a $C_1$~$C_{20}$ alkyl group;

$R_3$ and $R_4$ are each independently or simultaneously hydrogen, a hydroxy group, a $C_1$~$C_{20}$ alkoxide, a halogen atom, or a $C_1$~$C_{20}$ alkyl group;

$R_5$ is hydrogen, a $C_1$~$C_{20}$ alkyl, a cyclopropyl, or an aromatic $C_1$~$C_{20}$ hydrocarbon;

$R_6$ is hydrogen, sodium, potassium, or a $C_1$~$C_{150}$ alkyl group that comprises or does not comprise a polymerizable functional group;

$R_8$, $R_9$, and $R_{10}$ are each independently or simultaneously carbon or nitrogen; and $R_{11}$ is hydrogen, an amine (1°, 2°, 3°), a halogen atom, or a $C_1$~$C_{20}$ alkyl group.

Also, the invention provides a method of manufacturing the antimicrobial monomer compound of said formula 1 comprising the step of reacting a compound of the following formula 2:

[Formula 2]

wherein $R_1$~$R_6$ and $R_8$~$R_{11}$ are as defined in formula 1 above;

with a compound of the following formula 3:

R-Z  [Formula 3]

wherein R is as defined in formula 1 above and Z is a halogen atom, or a leaving group comprising a tosyl or a mesyl;

in the presence of a solvent with or without a base.

Also, the invention provides a method of manufacturing the antimicrobial monomer compound of said formula 1 comprising the epoxy ring-opening reaction of a compound of the following formula 2:

[Formula 2]

wherein $R_1$~$R_6$ and $R_8$~$R_{11}$, are as defined in formula 1 above;

with a compound of the following formula 3a:

[Formula 3a]

wherein $R_7$ is a saturated or unsaturated $C_1$ to $C_{148}$ hydrocarbon comprising a polymerizable functional group;

in the presence of a solvent with or without a base.

Also, the invention provides an antimicrobial homopolymer having an average molecular weight of 10,000~1,000,000 represented by the following formula 4:

[Formula 4]

wherein R, $R_1$~$R_6$, and $R_8$~$R_{11}$ are as defined in formula 1 above, and X is an integer greater than zero satisfying the above molecular weight.

Also, the invention provides a method of manufacturing the antimicrobial homopolymer of formula 4 comprising the step of radically polymerizing the antimicrobial monomer compound of formula 1 as defined above in the presence of an organic solvent and a catalyst (initiator).

Also, the invention provides an antimicrobial copolymer having an average molecular weight of 10,000~1,000,000 represented by the following formula 5:

[Formula 5]

wherein $R_1$~$R_6$, and $R_8$~$R_{11}$ are as defined in formula 1 above, m and n are each an integer greater than zero satisfying the above molecular weight, and Y is a monomer group capable of reacting a radically polymerizable functional group.

Also, the invention provides a method of manufacturing the antimicrobial copolymer of formula 5, comprising the step of radically copolymerizing the antimicrobial monomer compound of formula 1 with monomer Y having a polymerizable functional group in the presence of an organic solvent and a catalyst (initiator).

Also, the invention provides a method of manufacturing an antimicrobial polymeric compound comprising the steps of binding the antimicrobial monomer of formula 1 to a linker selected from the group consisting of an isocyanate class, a haloacylhalogenade and a compound containing an acid anhydride in the presence of an organic solvent, and then reacting it with a polyol.

Also, the invention provides an antimicrobial polymeric compound manufactured by the process as described above.

It is preferred that the above antimicrobial polymeric compound is selected from the group consisting of compounds represented by the following formula 6 to 9:

[Formula 6]

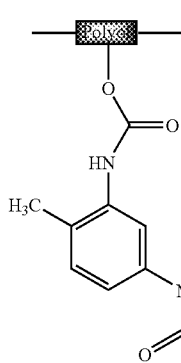

[Formula 7]

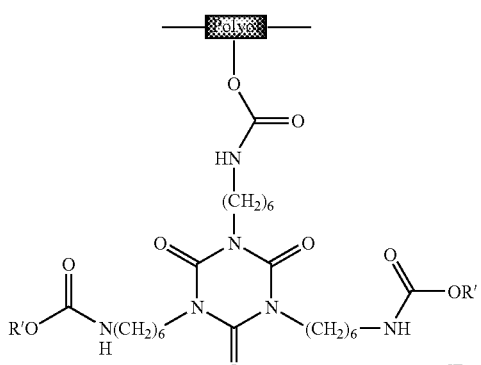

[Formula 8]

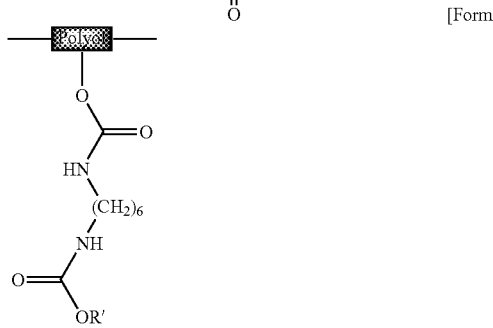

[Formula 9]

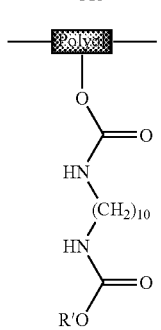

(in the formula 6 to 9, R' is a group represented by the following formula b:

[Formula b]

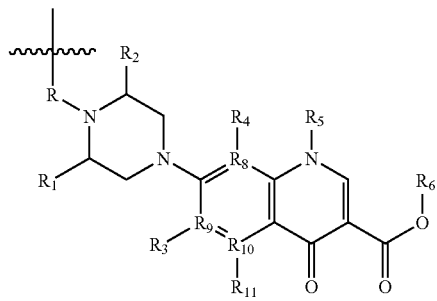

wherein R, $R_1$~$R_6$, and $R_8$~$R_{11}$ are as defined in formula 1 above.)

Also, the invention provides an antimicrobial acrylic copolymer having an average molecular weight of 10,000~1,000,000 represented by the following formula 10:

[Formula 10]

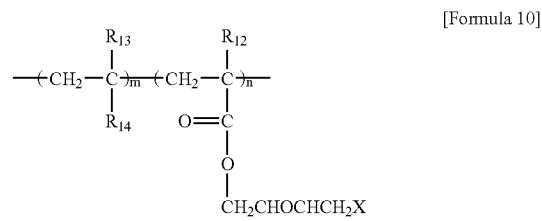

wherein $R_{12}$ and $R_{13}$ are each independently or simultaneously hydrogen or a methyl group, $R_{14}$ is a $C_1$~$C_{18}$ alkyl group comprising one or more selected from the group consisting of ester, carbonyl, amide, amine, cycloalkyl, ether, hydroxy, carboxylic acid, $C_2$~$C_{10}$ hetero ring containing N or O, sulfonyl, silane, lactone, and aldehyde groups, m and n are each an integer more than zero satisfying the above molecular weight, and X is a compound of the following formula 2a:

[Formula 2a]

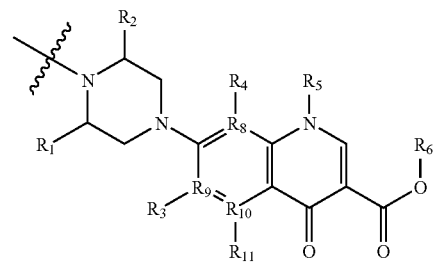

Also, the invention provides a method of manufacturing an antimicrobial acrylic copolymer of formula 10 comprising the step of radically polymerizing a compound of the following formula 11:

[Formula 11]

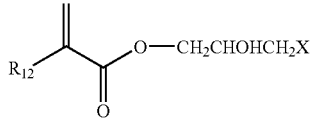

wherein $R_{12}$ is hydrogen or a methyl group, and
X is the compound of formula 2a as defined above;
with a compound of the following formula 12:

[Formula 12]

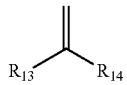

wherein $R_{13}$ is hydrogen or a methyl group, and
$R_{14}$ is a $C_1$~$C_{18}$ alkyl group comprising one or more selected from the group consisting of ester, carbonyl, amide, amine, cycloalkyl, ether, hydroxy, carboxylic acid, $C_2$~$C_{10}$ hetero ring containing N or O, sulfonyl, silane, lactone, and aldehyde groups.

Also, the invention provides an antimicrobial polymeric resin composition in which
a) a polymeric resin, and
b) one or more antimicrobial compounds selected from the group consisting of the antimicrobial monomer compound of formula 1, the antimicrobial homopolymer compound of formula 4, the antimicrobial copolymer compound of formula 5, the antimicrobial polymeric compounds of formula 6 to 9, and the acrylic copolymer of formula 10 are uniformly mixed.

Also, the invention provides a light-curable resin composition comprising an acrylic light-curable oligomer, a property-fortified monomer, a light initiator, and an additive,
in which the light-curable resin composition comprises one or more antimicrobial compounds selected from the group consisting of the antimicrobial monomer compound of formula 1, the antimicrobial homopolymer compound of formula 4, the antimicrobial copolymer compound of formula 5, the antimicrobial polymeric compounds of formula 6 to 9, and the acrylic copolymer of formula 10.

Also, the invention provides a molded and processed product comprising the polymeric resin composition. It is preferred that the molded and processed products are industrial supplies, various wrappers, consumer supplies or medical supplies, and they can be applied to interior materials such as blinds, wall papers and floor coverings; food related products such as films for wrapping, storage containers, and cutting boards; appliances such as humidifiers, washers, and dish washers; engineering materials such as water supply and drain pipes, and concrete; core materials in medical fields; and products for industrial purposes such as coatings. They are particularly useful for medical supplies, that is, medical devices/products for insertion into the human body such as catheters for medical purposes, prostheses, and products for repairing bones, or blood transfusion bags for medical purposes.

DETAILED DESCRIPTION OF THE PREFERRED EMBODIMENTS

The present invention is hereafter described in detail.

The inventors found a novel antimicrobial monomer during the process of researching polymeric substances with anti-microbial characteristics, verified that polymeric compounds manufactured from the above antimicrobial monomer using a light-curable, homopolymerizable/copolymerizable or intermediate-binding linker solved toxic problems due to elution, had durable anti-microbial effects and high heat resistance, and had high durability when manufactured into products, and thus completed the present invention.

In the present invention, R in formula 1 is preferably a saturated or unsaturated $C_1$~$C_{20}$ hydrocarbon comprising a light-curable reactive functional group and a polymerizable functional group, and R6, which comprises a polymerizable functional group, is preferably a $C_1$~$C_{20}$ alkyl group.

The above polymerizable functional group is one or more selected from the group consisting of carbon-carbon double bond (C═C) and carbon-carbon triple bond (C≡C), sulfonyl, halogen atom, nitro, hydroxy, thionyl (—SH), amine (1°, 2°, 3°), amide, amine, carbamate, oxime, carbonyl, carboxy, epoxy, acryl, ester, phenyl, vinyl, and nitrile groups.

Examples of the antimicrobial monomer compound of formula 1 of the present invention include 1-ethyl-6,8-difluoro-1,4-dihydro-7-[4-(2-hydroxy-6-methyl-4-oxa-5-oxo-6-heptenyl)-3-methyl-1-piperazinyl]-4-oxo-3-quinoline carboxylic acid, cis-5-amino-1-cyclopropyl-6,8-difluoro-1,4-dihydro-7-[4-(2-hydroxy-6-methyl-4-oxa-5-oxo-6-heptenyl)-3,5-dimethyl-1-piperazinyl]-4-oxo-3-quinoline carboxylic acid, 1-cyclopropyl-6-fluoro-7-[4-(3-dodecafluoro-2-hydroxy-4-oxaundecyl)-3-methyl-1-piperazinyl]-1,4-dihydro-5-methyl-4-oxo-3-quinoline carboxylic acid, 1-ethyl-6,8-difluoro-1,4-dihydro-7-{4-[2-hydroxy-3-(methoxy)phenoxypropyl]-3-methyl-1-piperazinyl}-4-oxo-3-quinoline carboxylic acid, 1-ethyl-6-fluoro-1,4-dihydro-7-{4-[2-hydroxy-3-(toluene-4-sulfonyloxy)-propyl]-1-piperazinyl}-4-oxo-3-quinoline carboxylic acid, 1-cyclopropyl-6-fluoro-1,4-dihydro-7-[4-(2-hydroxy-6-methyl-4-oxa-5-oxo-6-heptenyl)-1-piperazinyl]-4-oxo-3-quinoline carboxylic acid, etc.

The compound of formula 1 of the present invention can be manufactured by two methods as shown in scheme 1 and scheme 2, below.

First, the method according to scheme 1 is as follows:

Scheme 1

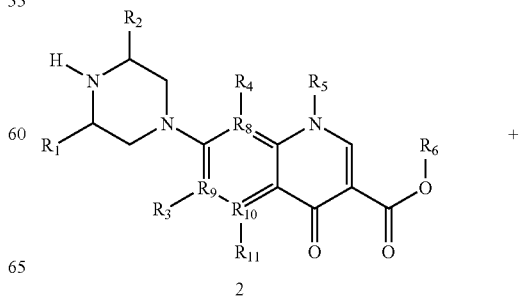

2

-continued

R—Z
3

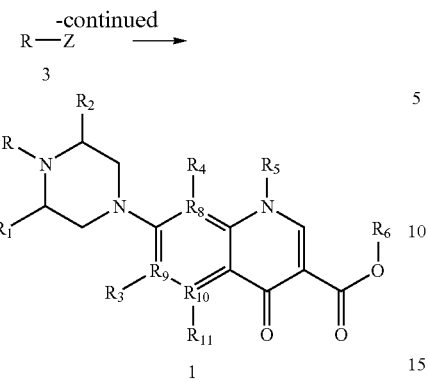

1

In the above scheme 1, R, $R_1$ to $R_{11}$, and Z are as defined above, and it is preferred that Z is generally a halogen atom —F, Cl, Br, or I— and a leaving group is a mesyl group (—OMs) or a tosyl group (—OTs).

In the present invention, the anti-microbial monomer of formula 1 is manufactured by reacting the compound of formula 2 with the compound of formula 3 as shown in the above scheme 1.

The ratios of the reaction compounds can be suitably adjusted, and it is preferred that the adding ratio of the compound of formula 3 with regard to the compound of formula 2 is 1:0.8 to 1:1.5 in terms of equivalent ratio.

The reaction temperature is not limited, but it is preferably −40 to 130° C. Also, to eliminate the acids that occur during the reaction, for example hydrogen chloride, a scavenger can be further added. As the scavenger, tetramethylguanidine, diethylamine, pyrrolidine, trimethylamine, triethylamine, pyridine or piperidine, calcium hydroxide, sodium hydroxide, calcium carbonate, potassium carbonate, and so on can be used alone or in a mixture of two or more kinds, and it is preferable to use the scavenger in an equivalent ratio of 1:1 to 1:3 with regard to the compound of formula 2.

Further, according to the present invention, the anti-microbial monomer compound of formula 1 can be manufactured by an epoxide ring-opening reaction of the compound of formula 2 with the compound of formula 3a, as shown in the following scheme 2:

Scheme 2

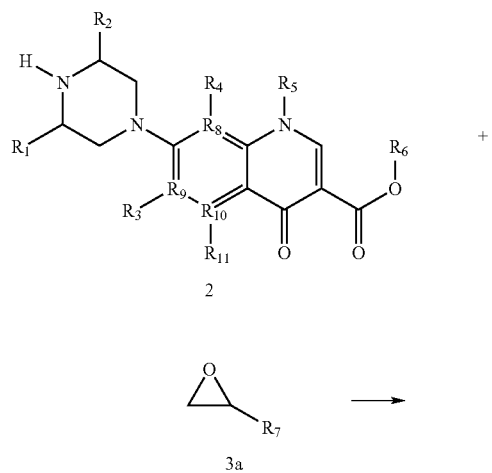

-continued

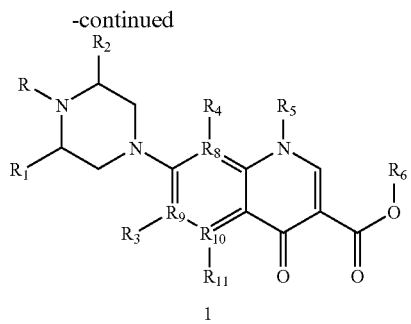

1

In the above scheme 2, R, $R_1$ to $R_{11}$, and Z are as defined above, and $R_7$ is a saturated or unsaturated $C_1$ to $C_{148}$ hydrocarbon comprising a polymerizable functional group. Preferably, $R_7$ is a saturated or unsaturated $C_1$~$C_{20}$ hydrocarbon comprising one or more functional groups selected from the group consisting of sulfonyl, halogen atom, nitro, hydroxy, thionyl (—SH), amine (1°, 2°, 3°), amide, imine, carbamate, oxime, carbonyl, carboxy, epoxy, acryl, ester, phenyl, vinyl, and nitrile groups.

The ratio of the reaction compounds is not limited, but it is preferably desirable that the equivalent ratio of the compound of formula 3a with regard to the compound of formula 2 is 1:0.8 to 1:4. Likewise, the reaction temperature is not limited, but it is preferably 35° C. to 150° C.

Both of the above reactions can be carried out in the presence of an individual organic solvent or a mixed organic solvent of two or more kinds. The organic solvent can be selected from the group of N,N-dimethylformamide, N,N-dimethylacetamide, dimethylsulfoxide, xylene, tetrahydrofuran, benzene, toluene, acetonitrile, dichloromethane, ethylacetate, butylacetate, 1,4-dioxane, and chloroform, but is not necessarily limited thereto.

The compound of formula 2 used in the above schemes 1 and 2 can be prepared according to the known methods, or it may be commercially available. Examples of the compound of formula 2 include 1-cyclopropyl-6-fluoro-1,4-dihydro-5-methyl-7-(3-methyl-1-piperazinyl)-4-oxo-3-quinoline carboxylic acid, 1-ethyl-6,8-difluoro-1,4-dihydro-7-(3-methyl-1-piperazinyl)-4-oxo-quinoline carboxylic acid, 8-ethyl-5,8-dihydro-2-(1-piperazinyl)-5-oxo-pyrido[2,3-d]pyrimidine-6-carboxylic acid, (cis)-5-amino-1-cyclopropyl-6,8-difluoro-1,4-dihydro-7-(3,5-dimethyl-1-piperazinyl)-4-oxo-3-quinoline carboxylic acid, 1-(2,4-difluorophenyl)-6-fluoro-1,4-dihydro-7-(3-methyl-1-piperazinyl)-4-oxo-3-quinoline carboxylic acid, 1-ethyl-6-fluoro-1,4-dihydro-7-(1-piperazinyl)-4-oxo-3-quinoline carboxylic acid, 1-cyclopropyl-6-fluoro-1,4-dihydro-7-(1-piperazinyl)-4-oxo-3-quinoline carboxylic acid, and salts thereof.

The compound of formula 3 and the compound of formula 3a can be prepared by the known methods. The compound of formula 3 is a halogen compound including acryloylchloride, methacryloylchloride, vinylchloride, or vinylbenzylchloride. Also, the compound of formula 3a is an epoxide derivative compound, and for example one or more compounds selected from the group of consisting of glyceroldiglycidylether, 2-methylacrylicacidoxyranylmethylester, glycidylnonylphenylether, glycidyldodecafluoroheptylether, glycidyl-4-methoxyphenylether, 2-methylacrylicacidoxyranylester, 2,3-epoxypropylmetharcrylate, 4-chlorophenylglycidylether, 1-chloro-2,3-epoxypropane, glycidylmethacrylate, glycidol, acrylicacidoxyranylmethylester, 2-aryloxymethyloxyrane, 2-pent-4-enyloxyrane, 2-vinyloxyrane, hexadecafluorononyloxymethyloxyrane, dodecafluoroheptyloxymethyloxyrane, octafluoropentyloxymethyloxyrane, 2-(4-nonylphenoxymethyl)oxyrane, 4-nitrobonzoicacidoxyranylmethylester, nitrobenzenesulfonicacidoxyranylmethylester, toluene4-sulfonicacidoxyranylmethylester, trityloxylmethyloxyrane, 1,3-bisoxyranylmethyoxypropane-2-olglycerolpropoxylatetriglycidylester, epichlorohydrine, and glycidoxypropyltrimethoxysilane can be used.

Also, the present invention provides an anti-microbial polymeric compound represented by a compound of the following formula 4:

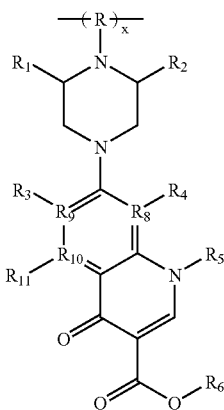

[Formula 4]

wherein R, $R_1$ to $R_6$, and $R_8$ to $R_{11}$ defined above; or a compound of the following formula 5:

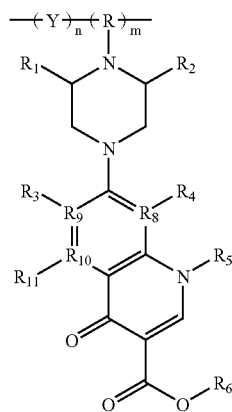

[Formula 5]

wherein R, $R_1$ to $R_6$, and $R_8$ to $R_{11}$, m, n, and Y are each as defined above using the anti-microbial monomer of formula 1. In the above formula 5, Y is preferably selected from the group consisting of a vinyl alcohol, acrylonitrile, butadiene, acrylic acid, styrene, acrylimide, methylmathacrylic acid, vinylchloride, vinylfluoride, an isocyanate class compound, vinyl acetate, and derivatives thereof.

The compound of formula 4 is a homo-polymer compound manufactured from the radical polymerization of a polymerizable functional group using the compound of formula 1 as a monomer. It is preferred that the compound of formula 4 has an average molecular weight of 10,000 to 1,000,000.

Also, the compound of formula 5 is an antimicrobial copolymer manufactured by the radical co-polymerization of the antimicrobial monomer compound of formula 1 with monomer Y having a polymerizable functional group. It is preferred that the compound of formula 5 has an average molecular weight of 10,000 to 1,000,000.

The manufacture of the compound of formula 4 and the compound of formula 5 of the present invention follows the following scheme 3:

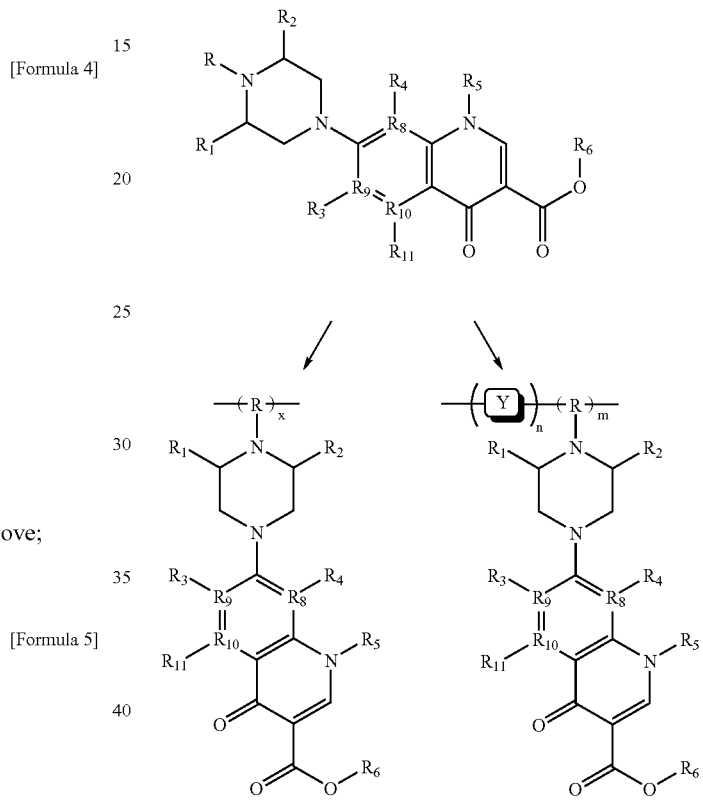

Scheme 3

The radical reaction to manufacture the compounds of formula 4 and 5 in the above scheme 3 is carried out by the addition of a conventional initiator.

As the initiator, any known initiators can be used, and for example, it is preferred that they are selected from the group consisting of azo-bis-iso-butylnitrile (AIBN), azobisdimethylbeleronitrile, benzoylperoxide, t-butylhydroperoxide, t-butylperoxyoctate, t-butylperoxybenzoate, cuminehydroperoxide, and cumylperoxide. All of the radical reactions of scheme 3 are performed in the presence of a solvent, and preferably the solvent can be one or more compounds selected from the group consisting of N,N-dimethylformamide, N,N-dimethylacetamide, dimethylsulfoxide, xylene, tetrahydrofuran, benzene, toluene, acetonitrile, dichloromethane, ethylacetate, butylacetate, 1,4-dioxane, and chloroform. Also, in the manufacture of the compound of formula 5, monomer Y with regard to the compound of formula 1 can be reacted in a ratio of 1:1 to 1:100.

Also, the present invention provides other antimicrobial polymeric compounds by binding the antimicrobial monomer of formula 1 to a linker and then reacting it with a polyol.

It is preferred that the antimicrobial polymeric compounds are compounds represented by formula 6 to 9 below, comprising a linker.

The linker is preferably selected from the group consisting of a compound of acid anhydride, haloacylhalogenade, and isocyanate (—N=C=O) classes. It is preferred that the isocyanate class linker is typically selected from the group consisting of toluenediisocyanate (TDI), dodecylisocyanate (DDI), hexamethylenediisocyanate (HDI), and trihexamethyleneisocyanuratetriisocyanate

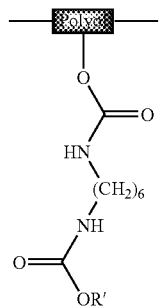

6

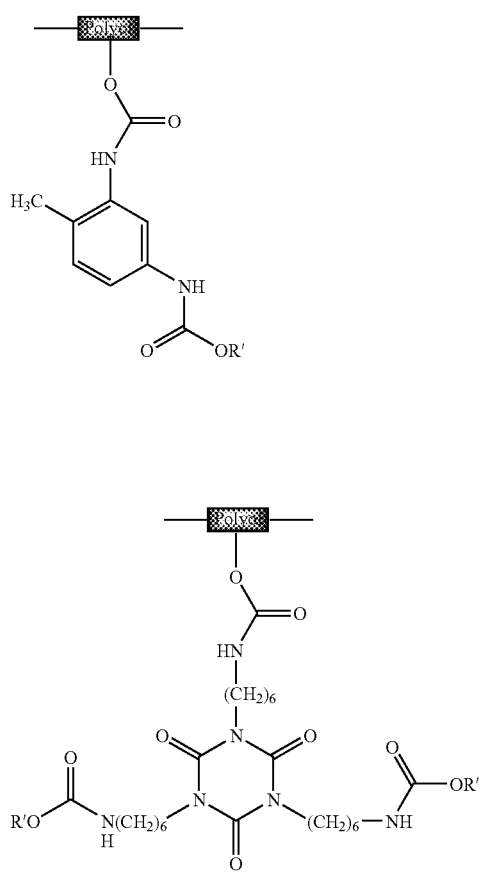

7

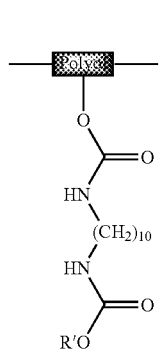

8

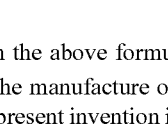

9

In the above formula 6 to 9, R' is as defined above.

The manufacture of the compounds of formula 6 to 9 of the present invention is performed by chemically binding the functional group of the compound of formula 1 to the isocyanate group of the linker and then binding it to a commonly-used polyol, as shown in scheme 4 and scheme 5, below. Typical polyols include BURNOCK (Aekyung Chemical, Co., Ltd.), ALKYLATE (Aekyung Chemical, Co., Ltd.), 045-093 (Aekyung Chemical, Co., Ltd.), Acryl (Kukdo Chemical, Co., Ltd.), Alkyde class polyol (Kukdo Chemical, Co., Ltd.), etc.

Scheme 4

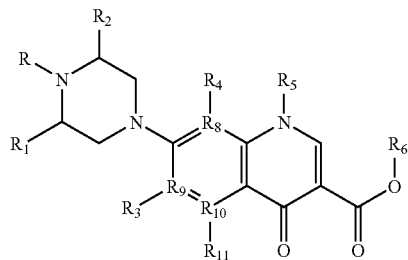

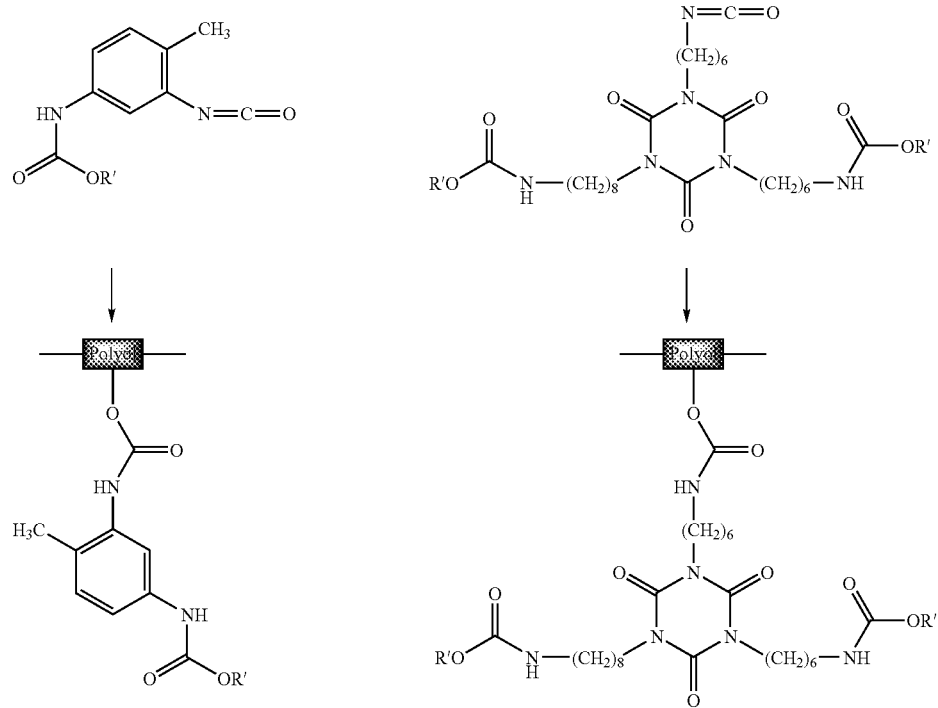
Scheme 5
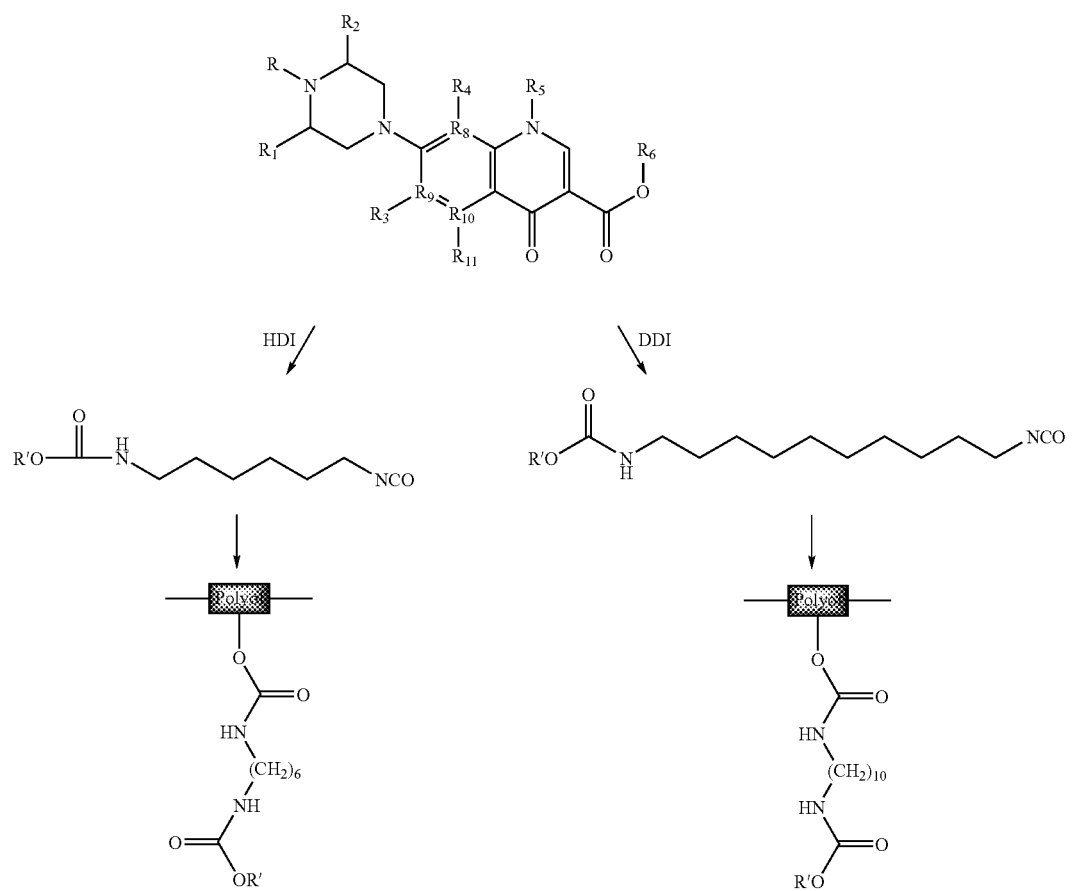

All of the above reactions are performed in the presence of a solvent, which is one or more compounds selected from the group consisting of N,N-dimethylformamide, N,N-dimethylacetamide, dimethylsulfoxide, xylene, tetrahydrofuran, benzene, toluene, acetonitrile, dichloromethane, ethylacetate, butylacetate, 1,4-dioxane, and chloroform.

A preferred embodiment of manufacture of the anti-microbial monomers and anti-microbial polymers of the present invention is as follows.

The compound of formula 1, which will be illustrated, is 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid.

That is, in formula 1,

R is an alkyl group comprising a hydroxy group, an ester bond, and a double bond of 7 carbon atoms (CH2=C(CH3)—CO—O—CH2-CH(OH)—CH—);

$R_1$ and $R_2$ are H;
$R_3$ is F;
$R_4$ is H;
$R_5$ is an ethyl group;
$R_6$ is H;
$R_8$, $R_9$, and $R_{10}$ are each C; and
$R_{11}$ is H.

(1) Manufacture of 1-Ethyl-6-Fluoro-1,4-Dihydro-7-[4-(2-Hydroxy-6-Methyl-4-Oxa-5-Oxo-6-Heptenyl)-1-Piperazinyl]-4-Oxo-3-Quinoline Carboxylic Acid 1-Ethyl-6-fluoro-1,4-dihydro-7-(1-piperazinyl)-4-oxo-3-quinoline carboxylic acid, which is the compound of formula 2, and glycidylmethacrylate, which is the compound of formula 3a, are heated at 70 to 80° C. and subjected to epoxide ring-opening reaction to thereby manufacture 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid (hereinafter referred to as "Compound A").

(2) Manufacture of Compound of Formula 4 (Anti-Microbial Polymer)

The initiator, benzoylperoxide, is added to the above compound A in the presence of N,N-dimethylformamide, and the radical polymerization is conducted at 70 to 80° C. to thereby manufacture the anti-microbial polymer.

(3) Manufacture of Compound of Formula 5 (Antimicrobial Polymer)

The above compound A is radically copolymerized with a methylmethacrylate monomer to thereby manufacture the compound of formula 5, poly(A-co-methylmethacrylate).

(4) Manufacture of Compounds of Formula 6 to 9 (Antimicrobial Polymer)

Compound A is reacted with toluenediisocyanate (TDI), dodecyldiisocyanate (DDI), hexamethylenediisocyanate (HDI), or trihexamethyleneisocyanuratetriisocyanate (HMTI) in an equivalent ratio of 1:1.5, mixed with a polyol selected from BURNOCK, ALKYLATE, 045-093, etc., and reaction is performed with the temperature change of 20 to 150° C. to thereby manufacture the antimicrobial polymers.

Also, the present invention provides an acrylic copolymer of formula 10 using a compound of formula 11 manufactured using the compound of formula 2.

The acrylic copolymer of formula 10 of the present invention can be manufactured by the radical reaction of the compound of formula 11 with the compound of formula 12 below (Scheme 6).

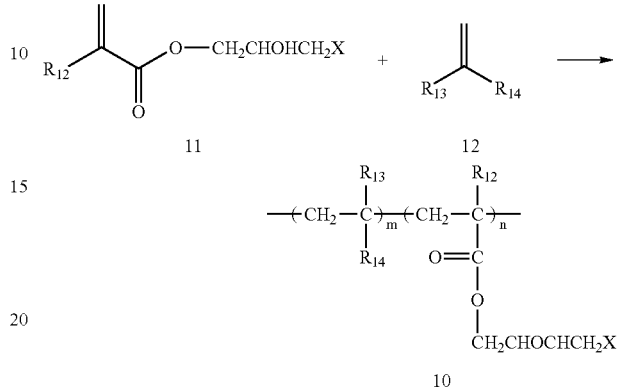

In the above scheme 6, R12 to R14 and X are each as defined above.

The compound of formula 11 can be obtained by epoxide ring-opening reaction of the compound of formula 2 with an epoxide compound having a double bond. The epoxide compound having a double bond is typically glycidylmethacrylate.

It is preferred that the compound of formula 12 has an acrylic monomer, which is the hydrocarbon chain attributed to an acrylic acid or methacrylic acid, as a main chain. More preferably, it is a monomer having an acrylic acid, acrylic acid alkyl ester, methacrylic acid, or methacrylic acid alkyl ester. The acrylic acid alkyl ester and methacrylic acid alkyl ester preferably include a $C_1$~$C_{18}$ alkyl. Examples of such acrylic acid alkyl ester include methylacrylate, ethylacrylate, n-propylacrylate, isopropylacrylate, cyclohexylacrylate, t-butylcyclohexylacrylate, stearylacrylate, and laurylacrylate. Also, the acrylic monomer can comprise a reactive functional group, and as examples of such functional groups, there are an amide group, a hydroxyl group, an epoxy group, a silanol group, and an aldehyde group. As acrylic monomers further comprising more specific reactive functional groups, there are acrylamide, metharcylamide, N-methylacrylamide, N-methylolacrylamide, N-butoxymethylacrylamide, N-methylmethacrylamide, N-butoxymethylmethacrylamide, hydroxyethylacrylate, hydroxyethylmethacrylate, hydroxypropylacrylate, hydroxypropylacrylate, hydroxypropylmethacrylate, glycidylacrylate, glycidylmethacrylate, y-trimethoxysilanemethacrylate, y-triethoxysilanemethacrylate, acrolein, caprolactone modified hydroxyacrylate, and caprolactone modified hydroxymethacrylate.

In the above scheme 6, any known initiators can be used, and they can be selected from the group consisting of azo-bis-iso-butylnitrile (AIBN), azobisdimethylbeleronitrile, benzoylperoxide, t-butylhydroperoxide, t-butylperoxyoctanate, t-butylperoxybenzoate, cuminehydroperoxide, and cumylperoxide. The initiators can be added in an amount of 0.05 to 10 parts by weight with regard to 100 parts by weight of the total compound, and preferably 0.3 to 5 parts by weight. The reaction temperature may be, but is not limited to, 50° C. to 130° C.

The compound of formula 1 and the polymeric compound comprising it of the present invention can be utilized for medical supplies, consumer goods, or products for industrial purposes. In particular, they can be applied to interior materials such as blinds, wall paper, and floor coverings; food-related products such as films for wrapping, containers for storing, and cutting boards; appliances such as humidifiers, washers, and dish washers; engineering materials such as water supply and drain pipes, and concrete; core materials in medical fields; and products for industrial purposes such as coatings. They can be particularly useful and they are preferably used in medical supplies, that is, medical devices/products for insertion into the human body such as catheters for medical purposes, artificial kidney apparatus, ventilating tubes for eardrums, cases for microbionic chip parts for insertion into a human body, prostheses, products for fixing bones, or for blood transfusion bags.

Therefore, the present invention provides an antimicrobial polymeric resin composition in which one or more antimicrobial polymers selected from the group consisting of the antimicrobial monomer compound of formula 1, the antimicrobial homopolymer of formula 4, the antimicrobial copolymer compound of formula 5, the compounds of formula 6 to 9, and the acrylic copolymer of formula 10 are uniformly mixed with an ordinary polymeric resin.

According to the present invention, the compound of formula 1 or polymeric compounds comprising it can be used as an additive for conventional polymeric resins to confer anti-microbial characteristics to the resins.

The antimicrobial polymeric resin comprising the antimicrobial compound of the present invention has a maximum release rate in water of 50 ppm/100 hrs, and preferably 10 ppm/100 hrs.

The antimicrobial compound can be included in an amount of 0.1 to 30% by weight with regard to the total composition, and the polymeric resin is included in the remaining amount.

The polymeric resins are preferably known polymeric resins, and for example, there are polyvinylalcohol, polyacrylonitrile, polybutadiene, polyacrylic acid, polyacrylimide, polysulfone, polyacetal, polyimide, polytetrafluoroethylene, polyneophrene, polydimethylsiloxane, polymethylmethacrylate, polyetheretherketone, polyphenylenesulfide, polyvinylfluoride, polyvinylacetate, polyetherimide, polyvinyllidinefluoride, polyethersulfone, urethane (urethane resin using isocyanates such as 2,4-toluenediisocyanate, trihexamethyleneisocyanuratetriisocyanate, etc.), silicon resin, and natural rubber.

Also, the present invention can use the above compounds in a combination of acrylic light-curable oligomers. That is, the invention can provide a light-curable resin composition comprising an acrylic light-curable oligomer, a property-fortified monomer, a light initiator, and an additive in which the light-curable resin composition comprises one or more antimicrobial polymers selected from the group consisting of the antimicrobial monomer compound of formula 1, the antimicrobial homopolymer of formula 4, the antimicrobial copolymer compound of formula 5, and the compounds of formula 6 to 9.

As the light-curable oligomer, acrylic resins having at least two or more acrylic groups are used, and particularly, urethane acrylate, polyester acrylate, epoxy acrylate, or silicon acrylate (Trademarks EB 284, 9269, 1290, 5129 of UCB Co.; CN 963, 966 of Sartomer Co., etc.) can be used.

As the property-fortified monomer, hydroxypropyl acrylate (HPA), 1,6-hexanedioldiacrylate (HDDA), pentaerythritol triacrylate (PETA), polyethyleneglycoldiacrylate (PEGDA), trimethylolpropane ethoxylate triacrylate (TMP-EOTA), or dipentaerythritol hexaacrylate (DPHA) can be used.

As the light initiator, 1-hydroxycyclohexylphenylketone (CibaGeigy, Irgacure 184) or Irgacure 500 in which Irgacure 184 is mixed with benzophenone in a ratio of 1:1 can be used.

As the additive for the improvement of smoothness, BYK 307 or BYK 310 (BYK Chemical) is used, and it can be used in an amount of 0.2 to 0.4% by weight based on the total resin. Also, as a diluent, ethanol, methanol, 2-propanol, butanol, or butylacetate can be used.

The antimicrobial polymeric resin compositions of the present invention can further comprise EBS or polyethylene wax as an additive when molded, and more preferably, it can comprise a polyethylene wax in an amount of 0.1 to 10% by weight.

Also, as methods for using the compound of formula 1 or the polymeric compound using it of the present invention in the polymeric resins, there are injection and extrusion molding, and blowing or laminating treatment methods after their direct addition during the molding process of plastics or their addition in the form of a master batch. Of them, the direct addition method includes steps of mixing the antimicrobial compounds with natural rubbers, synthetic rubbers, or polymeric resins, and then injection and extrusion molding, blowing, and laminate molding. The addition method in the form of a master batch includes the preparation of the master batch by mixing the antimicrobial substances with low-density polyethylene (LDPE), linear low-density polyethylene (LLDPE), high-density polyethylene (HDPE), polypropylene (PP), polyvinylchloride (PVC), polyurethane (PU), ABS, SAN, PCL, PC, silicon, or synthetic rubbers, and then extrusion molding; and the processes of mixing the above prepared master batch with an ordinary polymeric resin and injection and extrusion molding, blowing, and laminate molding.

It is preferred that the content of the compound of formula 1 or the polymeric compounds comprising it used in the preparation of the master batch is 0.1 to 30 parts by weight with regard to 100 parts by weight of the total composition. If the content of the compound of formula 1 or the polymeric compounds comprising it is less than 0.1 parts by weight, the anti-microbial effects are insignificant, and if it exceeds 30 parts by weight, the properties might not be good.

Hereafter, the examples of the present invention will be described. The following examples are provided solely to illustrate the present invention: the protection scope of the present invention is not limited thereto.

EXAMPLE 1

Manufacture of {1-Cyclopropyl-6-Fluoro-1,4-Dihydro-7-[4-(10,11-Epoxy-2,6-Dihydroxy-4,8-Dioxaundecyl)-3-Methyl-1-Piperazinyl]-5-Methyl-4-Oxo-3-Quinoline Carboxylic Acid}

15.0 ml of N,N-dimethylformamide were charged into a round 3-neck flask of 50 ml equipped with a thermometer and a stirring device, and 30.4 mg of 1-cyclopropyl-6-fluoro-1,4-dihydro-5-methyl-7-(3-methyl-1-piperazinyl)-4-oxo-3-quinoline carboxylic acid were added thereto and they were slowly stirred at room temperature for 10 minutes. 17.2 mg of glyceroldiglycidylether were added thereto and stirred. The reactants were washed with 1.2 ml of N,N-dimethylformamide, and they were reacted for 5 hours after their temperature was adjusted to 60° C. Thereafter, after cooling, they were stirred at 20° C. for 10 minutes. The reactants were obtained in a crystalized state from the layer of water and then dried to give 35.0 mg of 1-cyclopropyl-6-fluoro-1,4-dihydro-7-[4-(10,11-epoxy-2,6-dihydroxy-4,8-dioxaundecyl)-3-methyl-1-piperazinyl]-5-methyl-4-oxo-3-quinoline carboxylic acid.

$^1$H-NMR (DMSO-d$_6$) δ 1.05 (3H, d), 1.20~1.44 (4H, m), 2.40 (3H, s), 2.50~3.00 (7H, m), 3.10~4.00 (16H, m), 7.39 (1H, d), 8.81 (1H, s).

EXAMPLE 2

Manufacture of {1-Ethyl-6,8-Difluoro-1,4-Dihydro-7-[4-(2-Hydroxy-6-Methyl-4-Oxa-5-Oxo-6-Heptenyl)-3-M ethyl-1-Piperazinyl]-4-Oxo-3-Quinoline Carboxylic Acid}

39.4 mg of 1-ethyl-6,8-difluoro-1,4-dihydro-7-(3-methyl-1-piperazinyl)-4-oxo-3-quinoline carboxylic acid were mixed with 10.0 ml of 2,6-dimethylpiperazine in a round flask of 50 ml and slowly stirred at room temperature for 10 minutes. 22.0 mg of glycidylmethacrylate were added thereto and stirred at room temperature, and then the reactants were washed with 2.0 ml of 2,6-dimethylpiperazine. Thereafter, the reaction was performed at 40° C. for 8 hours, and after the temperature was reduced to room temperature, the reaction was performed for another 8 hours. The crystalized reactants were obtained from the layer of water and dried to give 25 mg of 1-ethyl-6,8-difluoro-1,4-dihydro-7-[4-(2-hydroxy-6-methyl-4-oxa-5-oxo-6-heptenyl)-3-methyl-1-piperazinyl]-4-oxo-3-quinoline carboxylic acid.

$^1$H-NMR (DMSO-d$_6$) δ 1.10 (3H, d), 1.58 (3H, t), 1.93 (3H, s), 2.52~3.00 (5H, m), 3.23~3.41 (4H, m), 3.90~4.38 (5H, m), 5.58 (1H, d), 6.15 (1H, d), 7.72 (1H, s), 8.62 (1H, s)

EXAMPLE 3

Manufacture of {8-Ethyl-5,8-Dihydro-2-{4-[2-Hydroxy-3-(4-Nonylphenoxy)Propyl]-1-Piperazinyl}-5-Oxopyrido[2,3-d]Pyrimidine-6-Carboxylic Acid}

38.0 mg of 8-ethyl-5,8-dihydro-5-oxo-2-(1-piperazinyl) pyrido{2,3-d}pyrimidine-6-carboxylic acid were mixed with 12.0 ml of dimethylsulfoxide in a round flask of 50 ml and slowly stirred at room temperature for 10 minutes. 18.0 mg of glycidylnonylphenylether were added thereto, it was stirred again at room temperature, and then washed with 12 ml of dimethylsulfoxide. The reactants were placed at 50° C. for 11 hours, and then stirred at 20° C. for 10 minutes. The reactants were crystalized from isopropyl alcohol and the layer of water with methylene chloride, filtered, and then dried to give 37.2 mg of 8-ethyl-5,8-dihydro-2-{4-[2-hydroxy-3-(4-nonylphenoxy)propyl]-1-piperazinyl}-5-oxo pyrido[2,3-d]pyrimidine-6-carboxylic acid.

$^1$H-NMR (DMSO-d$_6$) δ 0.88 (3H, t), 1.10~1.70 (17H, m), 2.45~3.05 (10H, m), 3.35~3.55 (4H, m), 3.92~4.12 (3H, m), 6.76, 7.05 (4H, ABq), 8.58 (1H, s), 8.87 (1H, s).

EXAMPLE 4

Manufacture of {Cis-5-Amino-1-Cyclopropyl-6,8-Difluoro-1,4-Dihydro-7-[4-(2-Hydroxy-6-Methyl-4-Oxa-5-Oxo-6-Heptenyl)-3,5-Dimethyl-1-Piperazinyl]-4-Oxo-3-Quinoline Carboxylic Acid}

43.7 mg of cis-5-amino-1-cyclopropl-6,8-difluoro-1,4-dihydro-7-(3,5-dimethyl-1-piperazinyl)-4-oxo-3-quinoline carboxylic acid were mixed with 5.0 ml of N,N-dimethylacetamide in a round flask of 50 ml and slowly stirred at room temperature for 10 minutes. 17.5 mg of glycidylmethacrylate were added thereto, it was stirred at room temperature, and then washed with 3.1 ml of N,N-dimethylacetamide. The reactants were held at 75° C. for 6 hours and then stirred at 20° C. for 10 minutes. Thereafter, the reactants were crystalized from isopropyl alcohol and the layer of water with methylene chloride, filtered, and then dried to give 29.3 mg of cis-5-amino-1-cyclopropyl-6,8-difluoro-1, 4-dihydro-7-[4-(2-hydroxy-6-methyl-4-oxa-5-oxo-6-heptenyl)-3,5-dimethyl-1-piperazinyl]-4-oxo-3-quinoline carboxylic acid.

$^1$H-NMR (DMSO-d$_6$) δ 1.07 (6H, d), 1.20~1.45 (4H, m), 1.96 (3H, s), 2.50~3.00 (4H, m), 3.20~3.60 (5H, m), 4.00~4.40 (3H, m), 5.67 (1H, s), 6.20 (1H, s), 8.60 (1H, s).

EXAMPLE 5

Manufacture of {1-(2,4-Difluorophenyl)-6-Fluoro-1, 4-Dihydro-7-[4-(2-Hydroxy-5-Methyl-4-Oxa-5-Oxo-6-Heptenyl)-3-Methyl-1-Piperazinyl]-4-Oxo-3-Quinoline Carboxylic Acid}

49.2 mg of 1-(2,4-difluorophenyl)-6-fluoro-1,4-dihydro-7-(3-methyl-1-piperazinyl)-4-oxo-3-quinoline carboxylic acid were mixed with 10.0 ml of N,N-dimethylformamide in a round flask of 50 ml and stirred at room temperature for 10 minutes. 14.3 mg of glycidylmethacrylate were added thereto, it was stirred at room temperature, and then washed with 5.0 ml of N,N-dimethylformamide. The reactants were held at 80° C. for 9 hours and then stirred at 20° C. for 10 minutes. The reactants were filtered as a crystal from isopropyl alcohol and the layer of water after application of methylene chloride, and then dried to give 41.0 mg of 1-(2,4-difluorophenyl)-6-fluoro-1,4-dihydro-7-[4-(2-hydroxy-5-methyl-4-oxa-5-oxo-6-heptenyl)-3-methyl-1-piperazinyl]-4-oxo-3-quinoline carboxylic acid.

$^1$H-NMR (DMSO-d$_6$) δ 1.06 (3H, d), 1.95 (3H, s), 2.50~3.00 (5H, m), 3.20~3.40 (4H, m), 4.00~4.40 (3H, m), 5.58 (1H, s), 6.15 (1H, s), 6.45~6.85 (4H, m), 7.89 (1H, d), 8.62 (1H, s).

EXAMPLE 6

Manufacture of {1-Cyclopropyl-6-Fluoro-7-[4-(3-Dodecafluoro-2-Hydroxy-4-Oxaundecyl)-3-Methyl-1-Piperazinyl]-1,4-Dihydro-5-Methyl-4-Oxo-3-Quinoline Carboxylic Acid}

39.4 mg of 1-cyclopropyl-6-fluoro-5-methyl-1,4-dihydro-7-(3-methyl-1-piperazinyl)-4-oxo-3-quinoline carboxylic acid were added to 12.2 ml of N,N-dimethylformamide in a round flask of 50 ml and slowly stirred at room temperature for 10 minutes. 37.3 mg of glycidyldodecafluoroheptylether were added thereto, it was stirred at room temperature, and then washed with 12.2 ml of N,N-dimethylformamide. The reactants were held at 70° C. for 6 hours and then stirred at 20° C. for 10 minutes. The reactants were crystalized from isopropyl alcohol and the layer of water with ether, filtered, washed with hexane, and then dried to give 43.1 mg of 1-cyclopropyl-6-fluoro-7-[4-(3-dodecafluoro-2-hydroxy-4-oxaundecyl)-3-methyl-1-piperazinyl]-1,4-dihydro-5-methyl-4-oxo-3-quinoline carboxylic acid.

$^1$H-NMR (DMSO-d$_6$) δ 1.06 (3H, d), 1.20~1.45 (4H, m), 2.40 (3H, s), 2.50~3.00 (5H, m), 3.20~4.10 (10H, m), 5.80~6.20 (1H, m) 7.40 (1H, d), 8.82 (1H, s).

EXAMPLE 7

Manufacture of {1-Ethyl-6,8-Difluoro-1,4-Dihydro-7-{4-[2-Hydroxy-3-(Methoxy)Phenoxypropyl]-3-Methyl-1-Piperazinyl]-4-Oxo-3-Quinoline Carboxylic Acid]

30.4 mg of 1-ethyl-6,8-difluoro-1,4-dihydro-7-(3-methyl-1-piperazinyl)-4-oxo-3-quinoline carboxylic acid were mixed with 13.0 ml of N,N-dimethylformamide in a round flask of 50 ml and slowly stirred at room temperature for 10 minutes. 19.7 mg of glycidyl-4-methoxyphenylether were added thereto, it was stirred at room temperature, and then washed with 10.2 ml of N,N-dimethylformamide. The reactants were held at 80° C. for 7 hours and stirred at 15° C. for 5 minutes. Thereafter, the reactants were crystalized from the ethyl alcohol phase and the layer of water with dioxane, filtered, washed with hexane and then dried to give 17.3 mg of 1-ethyl-6,8-difluoro-1,4-dihydro-7-{4-[2-hydroxy-3-(methoxy)phenoxypropyl]-3-methyl-1-piperazinyl}-4-oxo-3-quinoline carboxylic acid.

$^1$H-NMR (DMSO-$d_6$) δ 1.06(3H, d), 1.58 (3H, t), 2.50~3.00 (5H, m), 3.20~3.40 (4H, m), 3.70 (3H, s), 3.90~4.40 (5H, m), 6.60~6.80 (4H, m), 7.68 (1H, s), 8.60 (1H, s).

EXAMPLE 8

Manufacture of {1-Ethyl-6-Fluoro-1,4-Dihydro-7-{4-[2-Hydroxy-3-(Toluene-4-Sulfonyloxy)-Propyl]-1-Piperazinyl}-Oxo-3-Quinoline Carboxylic Acid}

39.4 mg of 1-ethyl-6-fluoro-1,4-dihydro-7-(1-piperazinyl)-4-oxo-3-quinoline carboxylic acid were mixed with 50 ml of N,N-dimethylformamide in a round flask of 100 ml and slowly stirred at room temperature for 20 minutes. 14.4 mg of glycidyl tosylate were added thereto, it was stirred at room temperature, and then washed with 30.0 ml of N,N-dimethylformamide. The reactants were held at 80° C. for 5 hours and then stirred at 25° C. for 10 minutes. The reactants were crystalized through column chromatography (20 gm silica, 10% ethylacetate/hexane), filtered, and then dried to give 11.2 mg of 1-ethyl-6-fluoro-1,4-dihydro-7-{4-[2-hydroxy-3-(toluene-4-sulfonyloxy)-propyl]-1-piperazinyl}-4-oxo-3-quinoline carboxylic acid.

$^1$H-NMR (DMSO-$d_6$) δ 1.60 (3H, t), 2.40 (3H, s), 2.50~2.85 (6H, m), 3.20~3.40 (4H, m), 3.90~4.40 (5H, m), 6.82 (1H, d), 7.40~7.85 (5H, m), 8.60 (1H, s).

EXAMPLE 9

Manufacture of {1-Cyclopropyl-6-Fluoro-1,4-Dihydro-7-[4-(2-Hydroxy-6-Methyl-4-Oxa-5-Oxo-6-Heptenyl)-1-Piperazinyl]-4-Oxo-3-Quinoline Carboxylic Acid}

39.4 mg of 1-cyclopropyl-6-fluoro-1,4-dihydro-7-(1-piperazinl)-4-oxo-3-quinoline carboxylic acid were mixed with 50 ml of N,N-dimethylacetamide in a round flask of 100 ml and slowly stirred at room temperature for 30 minutes. 17.5 mg of glycidylmethacrylate were added thereto, it was stirred at room temperature, and then washed with 1.2 ml of N,N-dimethylacetamide. Thereafter, the reactants were held at 80° C. for 19 hours, stirred at 25° C. for 30 minutes, and then crystalized from isopropyl alcohol and the layer of water with methylene chloride and filtered. The filtrates were dried to give 53.3 mg of 1-cyclopropyl-6-fluoro-1,4-dihydro-7-[4-(2-hydroxy-6-methyl-4-oxa-5-oxo-6-heptenyl)-1-piperazinyl]-4-oxo-3-quinoline carboxylic acid.

$^1$H-NMR (CDCl$_3$) δ 1.20~1.41 (4H, m), 2.05 (3H, s), 2.51 (2H, d), 2.59 (2H, t), 2.85 (2H, d), 3.25~3.60 (5H, m), 4.05 (2H, m), 4.30 (1H, m), 5.58 (1H, s), 6.15 (1H, s), 7.28 (1H, d), 8.05 (1H, d), 8.80 (1H, s)

EXAMPLE 10

Manufacture of {1-Ethyl-6-Fluoro-1,4-Dihydro-7-[4-(2-Hydroxy-6-Methyl-4-Oxa-5-Oxo-6-Heptenyl)-1-Piperazinyl]-4-Oxo-3-Quinoline Carboxylic Acid}

39.4 mg of 1-ethyl-6-fluoro-1,4-dihydro-7-(1-piperazinyl)-4-oxo-3-quinoline carboxylic acid were added to 50 ml of N,N-dimethylacetamide in a round flask of 100 ml and slowly stirred at room temperature for 10 minutes. 17.5 mg of glycidylmethacrylate were added thereto, it was stirred at room temperature, and then washed with 11.2 ml of N,N-dimethylacetamide. Thereafter, the reactants were held at 80° C. for 15 hours and then stirred at 25° C. for 1 hour. The reactants were passed through column chromatography (20 gm silica, 10% ethylacetate/hexane), crystalized from isopropylalcohol and the layer of water with methylene chloride, and then filtered. The filtrates were dried to give 36 mg of 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid.

$^1$H-NMR (CDCl$_3$) δ 1.48 (3H, t), 1.93 (3H, s), 2.51 (2H, d), 2.59~2.82 (4H, m), 3.10~3.40 (4H, t), 3.45 (2H, m), 3.90~4.28 (4H, m), 5.58 (1H, d), 6.05 (1H, d), 6.75 (1H, S), 7.62 (1H, d), 8.58 (1H, s)

EXAMPLE 11

Manufacture of {8-Ethyl-5,8-Dihydro-2-[4-(2-Hydroxy-6-Methyl-4-Oxa-5-Oxo-6-Heptenyl)-1-Piperazinyl]-5-oxo-Pyrido[2,3-d]Pyrimidine-6-Carboxylic Acid}

38.2 mg of 8-ethyl-5,8-dihydro-5-oxo-2-(1-piperazinyl)-pyrido[2,3-d]pyrimidine-6-carboxylic acid were mixed with 50 ml of N,N-dimethylacetamide in a round flask of 100 ml and slowly stirred at room temperature for 50 minutes. 15.0 mg of glycidylmethacrylate were added thereto, it was stirred at room temperature, and then washed with 10 ml of N,N-dimethylacetamide. Thereafter, the reactants were held at 70° C. for 15 hours and then stirred at 20° C. for 1 hour. The reactants were passed through column chromatography (20 gm silica, 10% ethylacetate/hexane), crystalized from isopropyl alcohol and the layer of water with methylene chloride, filtered, and then dried to give 27 mg of 8-ethyl-5,8-dihydro-2-[4-(2-hydroxy-6-methyl-4-oxa-5-oxo-6-heptenyl)-1-piperazinyl]-5-oxo-pyrido[2,3-d]pyrimidine-6-carboxylic acid.

$^1$H-NMR (DMSO-$d_6$) δ 1.58 (3H, s), 1.95 (3H, s), 2.50~2.85 (6H, m), 3.20~3.50 (4H, m), 3.90~4.40 (5H, m), 5.60 (1H, s), 6.14 (1H, s), 8.62 (1H, s), 8.87 (1H, s).

EXAMPLE 12

Manufacture of {1-Ethyl-6-Fluoro-1,4-Dihydro-7-[4-(1-Oxo-2-Propenyl)-1-Piperazinyl]-4-Oxo-3-Quinoline Carboxylic Acid}

Under nitrogen conditions, 30 ml of chloroform were added to 500 mg (1.567 mmol) of 1-ethyl-6-fluoro-1,4- dihydro-7-(1-piperazinyl)-4-oxo-3-quinoline carboxylic acid in a round flask of 50 ml, into which 0.436 ml (3.134 mmol) of triethylamine was then charged and stirred at room temperature for 10 minutes. While the inside temperature of the container was maintained at −10° C., 0.127 ml (1.567 mmol) of acrylochloride was slowly dripped thereinto and reacted. The reaction was conducted under nitrogen at −10° C. for 3 hours, then distilled water was added to the reactants, which were then extracted with dichloromethane. The extracts were concentrated and then chromatographed (20 gm silica, 7% MeOH/CH2Cl2) to give 1-ethyl-6-fluoro-1,4-dihydro-7-[4-(1-oxo-2-propenyl)-1-piperazinyl]4-oxo-3-quinoline carboxylic acid.

$^1$H-NMR (CDCl$_3$) δ 1.48 (3H, t), 3.20 (4H, t), 3.42 (4H, t), 4.32 (2H, q), 5.55 (1H, t), 6.12 (1H, t), 6.62 (1H, t), 7.02 (1H, s), 7.75 (1H, s), 8.85 (1H, s)

EXAMPLE 13

Manufacture of {1-Cyclopropyl-6-Fluoro-1,4-Dihydro-7-[4-(2-Methyl-1-Oxo-2-Propenyl)-1-Piperazinyl]-4-Oxo-3-Quinoline Carboxylic Acid}

700 mg (2.024 mmol) of 1-cyclopropyl-6-fluoro-1,4-dihydro-7-(1-piperazinyl)-4-oxo-3-quinoline carboxylic acid were added to a round 3-neck flask of 50 ml under a nitrogen atmosphere, and then stirred at room temperature for 10 minutes after 30 ml of chloroform and 0.491 ml (3 mmol) of pyridine were added thereto. While the temperature of the inside of the container was kept at −10° C., 0.197 ml (2.024 mmol) of methacryloylchloride was slowly dripped thereinto. After reaction for 3 hours, distilled water was added to the reactants, which were then extracted with dichloromethane, concentrated, and chromatographed (20 gm silica, 7% MeOH/CH2Cl2) to give 1-cyclopropyl-6-fluoro-1,4-dihydro-7-[4-(2-methyl-1-oxo-2-propenyl)-1-piperazinyl]-4-oxo-3-quinoline carboxylic acid.

$^1$H-NMR (CDCl$_3$) δ 1.20 (2H, m), 1.41 (2H, m), 2.00 (3H, s), 3.30 (4H, t), 3.35 (1H, m), 3.50 (1H, m), 3.95 (2H, d), 5.20 (2H, d) 7.42 (1H, d), 8.00 (1H, d), 8.90 (1H, s)

EXAMPLE 14

Manufacture of {1-Ethyl-6-Fluoro-1,4-Dihydro-7-[4-(4-Vinylbenzyl)-1-Piperazinyl]-4-Oxo-3-Quinoline Carboxylic acid}

Under a nitrogen atmosphere, 400 mg (1.252 mmol) of 1-ethyl-6-fluoro-1,4-dihydro-7-(1-piperazinyl)-4-oxo-3-quinoline carboxylic acid were mixed with 0.349 ml (2.505 mmol) of triethylamine in a round flask of 50 ml and stirred at room temperature for 10 minutes. While the temperature of the inside of the container was kept at −10° C., 0.177 ml (1.252 mmol) of vinylbenzylchloride was slowly dripped thereinto. Under a nitrogen atmosphere, the reaction was conducted for three hours while keeping the temperature at −10° C., and then distilled water was added to the reactants which were then extracted with dichloromethane. The extracts were concentrated and then chromatographed (20 gm silica, 5% MeOH/CH2Cl2) to give 501 mg (91.9%) of 1-ethyl-6-fluoro-1,4-dihydro-7-[4-(4-vinylbenzyl)-1-piperazinyl]-4-oxo-3-quinoline carboxylic acid.

$^1$H NMR (CDCl$_3$) δ 1.48 (3H, t), 3.20 (4H, t), 3.42 (4H, t), 4.55 (2H, q), 5.18 (2H, s), 5.61 (2H, d), 6.63 (1H, m) 7.01 (2H, d), 7.10 (1H, d), 7.18 (2H, d), 7.81 (1H, d), 8.87 (1H, s)

EXAMPLE 15

Manufacture of Compound of Formula 4

750 mg of 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid were dissolved in 30 ml of N,N-dimethylacetamide in a round flask of 50 ml and stirred at room temperature for 10 minutes. 20 mg of AIBN were added to the reactants, which were then reacted at 70° C. for 4 hours and then cooled to room temperature. The resultant reactants were slowly added to 100 ml of cold water, which was prepared in advance, and then stirred at room temperature for 30 minutes and filtered to thereby yield crystals. They were dried to give the compound of formula 4.

EXAMPLE 16

Manufacture of Compound of Formula 5

0.5 g (1.251 mmol) of 1-cyclopropyl-6-fluoro-1,4-dihydro-7-[4-(2-hydroxy-6-methyl-4-oxa-5-oxo-6-heptenyl)-1-piperazinyl]-4-oxo-3-quinoline carboxylic acid were dissolved in 30 ml of N,N-dimethylformamide in a round flask of 50 ml and then stirred at room temperature for 10 minutes. 10 g (138.77 mmol) of acrylic acid were added to the reactants, which were then reacted at room temperature for 10 minutes, and then 0.05 g of benzoylperoxide was slowly dripped thereinto. Subsequently, after the temperature was raised to 80° C., the reaction was performed for 4 hours followed by cooling to room temperature. 100 ml of cold water, which was prepared in advance, was slowly added to the reactants while stirring, and the solids were filtered and dried to give the title compound.

EXAMPLE 17

Manufacture of Compound of Formula 5a 4.5 g (62.44 mmol) of acrylic acid were charged into a 500 ml 3-neck flask, 100 ml of toluene were added thereto, and then 0.5 g (1.083 mmol) of 1-cyclopropyl-6-fluoro-1,4-dihydro-7-[4-(2-hydroxy-6-methyl-4-oxa-5-oxo-6-heptenyl)-1-piperazinyl]-4-oxo-3-quinoline carboxylic acid of Example 9 was added. Under a nitrogen atmosphere, after the temperature was raised to 40° C., the reactants were stirred, 0.1 g of BPO was added thereto, and then the temperature was slowly raised to 80° C. again. The reactants were held at 80° C. for 2 hours and 40 minutes, cooled again to room temperature, and then filtered under a reduced pressure to thereby yield white solids. They were washed with ether and then dried to give 4.75 g of the antimicrobial acrylic acid copolymer (95% yield).

EXAMPLE 18

Manufacture of Compound of Formula 5a 15.6 g (216.6 mmol) of acrylic acid were charged into a 500 ml 3-neck flask, 100 ml of toluene were added thereto and dissolved, and then 10 g (21.66 mmol) of 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid of Example 10 were added thereto and stirred under a nitrogen gas condition after raising the temperature to 40° C. 0.5 g of AIBN was added thereto, and after the temperature was raised to 80° C., the reaction was conducted for 3 hours and 10 minutes while keeping the temperature at 80° C. The obtained white solids were filtered under a reduced pressure, washed with ether, and then dried to give 24.627 g of the antimicrobial acrylic acid copolymer (96.2% yield).

EXAMPLE 19

Manufacture of Compound of Formula 5b 15.6 g (119.8 mmol) of HEMA (2-hydroxyethylmethacrylate) and 50 ml of DMSO were charged into a 500 ml 3-neck flask, and 10.21 g (21.6 mmol) of 1-cyclopropyl-6-fluoro-1,4-dihydro-7-[4-(2-hydroxy-6-methyl-4-oxa-5-oxo-6-heptenyl)-1-piperazinyl]-4-oxo-3-quinoline carboxylic acid of Example 9 were added thereto and completely dissolved by heating it to 40° C. 0.5 g of AIBN were added to the dissolved reactants while stirring under a nitrogen gas condition, and the temperature was raised to 75° C. and then the reactants were placed for three hours. The produced light-yellow solids were filtered under a reduced pressure, washed with ether, and dried to give 25.16 g of the antimicrobial acrylic copolymer (97.66% yield).

EXAMPLE 20

Manufacture of Compound of Formula 5c 2 g (23.49 mmol) of methacrylicamide and 50 ml of DMF were charged into a 500 ml 3-neck flask, and then 5.42 g (11.44 mmol) of the compound of Example 9 were added thereto. 0.1 g of BPO was added to the reactants, which were then reacted under a nitrogen gas condition at 75° C. for three hours. The reactants were solidified in water, filtered under a reduced pressure, stirred three times with acetone 100 for 10 minutes, and then filtered and dried to give 7.22 g of the antimicrobial methacrylicamide copolymer in the form of light yellow solids (97.4% yield).

EXAMPLE 21

Manufacture of Compound of Formula 5d 5.0 g (58.74 mmol) of methacrylicamide and 70 ml of DMF were added to a 500 ml 3-neck flask in turn and completely dissolved. 2.71 g (5.874 mmol) of the compound of Example 10 and 0.19 g of BPO were added thereto and heated to 75° C. under a nitrogen gas condition while stirring. The reactants were reacted at 75° C. for 2 hours and 10 minutes and then cooled. 100 ml of toluene was added thereto to produce light yellow precipitates, which were then filtered under a reduced pressure and dried to give 7.60 g of the antimicrobial methacrylamide copolymer (98.6% yield).

EXAMPLE 22

Manufacture of Compound of Formula 5f 10 g (99.88 mmol) of methylmethacrylate and 360 ml of N,N-dimethylacetamide were added to a 500 ml 3-neck flask in turn and completely dissolved. Thereafter, 47.29 g (99.88 mmol) of the compound of Example 9 and 1.682 g of AIBN were added thereto while stirring under a nitrogen gas condition. After the temperature was raised to 75° C., the reaction was conducted for 6 hours, and then the temperature was cooled to room temperature and the reactants were solidified in 1000 ml of cold water. The solids were filtered under a reduced pressure, washed with 450 ml of acetone three times for 5 minutes, and then dried to give 54.69 g of the antimicrobial acrylic copolymer in the form of yellow solids (95.5% yield).

EXAMPLE 23

Manufacture of Compound of Formula 5g 10 g (99.88 mmol) of methylmethacrylate and 360 ml of N,N-dimethylacetamide were added to a 500 ml 3-neck flask in turn and completely dissolved. 47.292 g (99.88 mmol) of the compound of Example 10 and 1.7189 of AIBN were added thereto. Thereafter, the reactants were reacted while stirring under a nitrogen gas condition for 6 hours after the temperature was raised to 75° C. The reactants were cooled to room temperature and solidified in 1000 ml of cold water, and then filtered under a reduced pressure. The filtrates were washed with 450 ml of acetone three times for 5 minutes and dried to give 56.396 g of the antimicrobial acrylic copolymer in the form of yellow solids (98.43% yield).

Further, according to the same methods as in Examples 15 to 23 above, the compounds of formula 4 and 5 were manufactured respectively, using 1-ethyl-6,8-difluoro-1,4-dihydro-7-[4-(2-hydroxy-6-methyl-4-oxa-5-oxo-6-heptenyl)-3-methyl-1-piperazinyl]-4-oxo-3-quinoline carboxylic acid, cis-5-amino-1-cyclopropyl-6,8-difluoro-1,4-dihydro-7-[4-(2-hydroxy-6-methyl-4-oxa-5-oxo-6-heptenyl)-3,5-dimethyl-1-piperazinyl]-4-oxo-3-quinoline carboxylic acid, 1-(2,4-difluorophenyl)-6-fluoro-1,4-dihydro-7-[4-(2-hydroxy-5-methyl-4-oxa-5-oxo-6-heptenyl)-3-methyl-1-piperazinyl]-4-oxo-3-quinoline carboxylic acid, 1-cyclopropyl-6-fluoro-1,4-dihydro-7-[4-(2-hydroxy-6-methyl-4-oxa-5-oxo-6-heptenyl)-1-piperazinyl]-4-oxo-3-quinoline carboxylic acid, 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid, 8-ethyl-5,8-dihydro-2-[4-(2-hydroxy-6-methyl-4-oxa-5-oxo-6-heptenyl)-1-piperazinyl]-5-oxo-pyrido[2,3-d]pyrimidine-6-carboxylic acid, 1-ethyl-6-fluoro-1,4-dihydro-7-[4-(1-oxo-2-propenyl)-1-piperazinyl]-4-oxo-3-quinoline carboxylic acid, or 1-cyclopropyl-6-fluoro-1,4-dihydro-7-[4-(2-methyl-1-oxo-2-propenyl)-1-piperazinyl]-4-oxo-3-quinoline carboxylic acid, and using AIBN or benzoylperoxide as an initiator.

EXAMPLE 24

Manufacture of Linker-Binding Type Antimicrobial Monomer I 0.840 mg of 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid and 30 ml of benzene were charged into a 500 ml 3-neck and dissolved at 50° C., and then 0.635 mg of tolylene 2,4-diisocyanate and 0.01 mg of dibutyltindiolate (DBTDL) were added thereto and stirred at 60° C. for 2 hours. 0.213 mg of isopropylalcohol was added to the reactants, which were then stirred at 60° C. for 5 hours to thereby complete the reaction. After the reactants' temperature was cooled to room temperature, the reaction solvents were eliminated by distillation under a reduced pressure and the reaction products were chromatographed (20 mg silica, 10% ethylacetate/hexane) to give the antimicrobial compound.

EXAMPLE 25

Manufacture of Linker-Binding Type Antimicrobial Monomer II 2.2 mg of 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid and 100 ml toluene were charged into a 250 ml 3-neck, and dissolved at 80° C., and then 3.7 mg of trihexamethyleneisocyanuratetriisocyanate and 0.01 mg of dibutyltindiolate (DBTDL) were added thereto and reacted at 110° C. for 12 hours. 75 mg of isopropylalcohol were added to the reactants, which were stirred at 60° C. for 5 hours to thereby complete the reaction. After the reaction temperature was cooled to room temperature, the reaction solvents were eliminated by distillation under a reduced pressure and the reaction products were chromatographed (20 mg silica, 10% ethylacetate/hexane) to give the antimicrobial compound.

Further, according to the same methods as in Example 24 and 25 above, 1-cyclopropyl-6-fluoro-1,4-dihydro-7-[4-(10,11-epoxy-2,6-dihydroxy-4,8-dioxaundecyl)-3-methyl-1-piperazinyl]-5-methyl-4-oxo-3-quinoline carboxylic acid, 1-ethyl-6,8-difluoro-1,4-dihydro-7-[4-(2-hydroxy-6-methyl-4-oxa-5-oxo-6-heptenyl)-3-methyl-1-piperazinyl]-4-oxo-3-quinoline carboxylic acid, 8-ethyl-5,8-dihydro-2-{4-[2-hydroxy-3-(4-nonylphenoxy)propyl]-1-piperazinyl}-5-oxo pyrido[2,3-d]pyrimidine-6-carboxylic acid, cis-5-amino-1-cyclopropyl-6,8-difluoro-1,4-dihydro-7-[4-(2-hydroxy-6-methyl-4-oxa-5-oxo-6-heptenyl)-3,5-dimethyl-1-piperazinyl]-4-oxo-3-quinoline carboxylic acid, 1-(2,4-difluorophenyl)-6-fluoro-1,4-dihydro-7-[4-(2-hydroxy-5-methyl-4-oxa-5-oxo-6-heptenyl)-3-methyl-1-piperazinyl]-4-oxo-3-quinoline carboxylic acid, 1-cyclopropyl-6-fluoro-7-[4-(3-dodecafluoro-2-hydroxy-4-oxaundecyl)-3-methyl-1-piperazinyl]-1,4-dihydro-5-methyl-4-oxo-3-quinoline carboxylic acid, 1-ethyl-6,8-difluoro-1,4-dihydro-7-{4-[2-hydroxy-3-(methoxy)phenoxypropyl]-3-methyl-1-piperazinyl}-4-oxo-3-quinoline carboxylic acid, 1-ethyl-6-fluoro-1,4-dihydro-7-{4-[2-hydroxy-3-(toluene-4-sulfonyloxy)propyl]-1-piperazinyl}-4-oxo-3-quinoline carboxylic acid, 1-cyclopropyl-6-fluoro-1,4-dihydro-7-[4-(2-hydroxy-6-methyl-4-oxa-5-oxo-6-heptenyl)-1-piperazinyl]-4-oxo-3-quinoline carboxylic acid, 1-ethyl-6-fluoro-1,4-dihydro-7-[4-(2-hydroxy-6-methyl-4-oxa-5-oxo-6-heptenyl)-1-piperazinyl]-4-oxo-3-quinoline carboxylic acid, or 8-ethyl-5,8-dihydro-2-[4-(2-hydroxy-6-methyl-4-oxa-5-oxo-6-heptenyl)-1-piperazinyl]-5-oxo-pyrido[2,3-d]pyrimidine-6-carboxylic acid was bounded to toluenediisocyanate (TDI), dodecyldiisocyanate (DDI), hexamethylenediisocyanate (HDI), or trihexamethyleneisocyanuratetriisocyanate (HMTI), respectively, as a linker to manufacture the antimicrobial monomers.

EXAMPLE 26

Antimicrobial Polymer

Each of the compounds manufactured in Examples 24 and 25 above was combined or reacted with the polyols of Table 1 below to manufacture the antimicrobial polymers (yield: 100%). The reaction temperature was varied according to the polyols used, within the range of room temperature or 50° C. to 150° C.

TABLE 1

| | Acrylate and Alkydpolyol Copolymer | | | |
|---|---|---|---|---|
| Category | OH Value (%) | Tg (° C.) | NVM(%) | |
| Burnock* | 17.5 | 126 | 50 | Burnock: Acrylpolyol |
| ALKYLATE* | 25 | 79 | 50 | ALKYLATE: Acrylpolyol |
| 045-093* | 80 | 97 | 55 | Kukdo Chemical, |
| Kukdo Chemical, Co. | 23 | 89 | 50 | Co.: Acrylpolyol 045-093: Alkydpolyol |

EXAMPLE 27

Manufacture of Antimicrobial Light-Curable Resin

Light-curable oligomers, property-fortified monomers, light initiators, and additives for the improvement of smoothness were added to the antimicrobial monomer compounds or antimicrobial polymers to manufacture the light-curable resins.

As the light-curable oligomer, an acrylic resin having at least two or more acrylic groups was used, and particularly, urethane acrylate, polyester acrylate, epoxy acrylate, or silicon acrylate was used (Trademarks: EB 284, 9269, 1290, 5129 of UCB Co.; CN 963, 966 of Sartomer Co., etc.).

As the property-fortified monomer, hydroxypropyl acrylate (HPA), 1,6-hexanedioldiacrylate (HDDA), pentaerythritol triacrylate (PETA), polyethyleneglycoldiacrylate (PEGDA), trimethylolpropane ethoxylate triacrylate (TMPEOTA), or dipentaerythritol hexaacrylate (DPHA) was used.

As the light initiator, 1-hydroxycyclohexylphenylketone (CibaGeigy, Irgacure 184) or Irgacure 500 in which Irgacure 184 and benzophenone were mixed in a ratio of 1:1 was used.

As the additive for the improvement of smoothness, BYK 307 or BYK 310 (BYK Chemical) was used in an amount of 0.2 to 0.4% by weight of the total resin. Also, as the diluent, ethanol, methanol, 2-propanol, butanol, or butylacetate was used.

Table 2 below (units: wt. %) shows the ratios of the components contained in the light-curable resins.

TABLE 2

| Components | Resin 1 | Resin 2 | Resin 3 | Resin 4 | Resin 5 | Resin 6 |
|---|---|---|---|---|---|---|
| EB9269 | 55 | 50 | — | 45 | 45 | — |
| EB1290 | — | — | 40 | — | — | 40 |
| DPHA | — | — | 10 | — | — | 10 |
| PETA | 15 | 5 | 10 | 5 | 5 | 10 |
| HDDA | 15 | 15 | 10 | 15 | 15 | 10 |
| HPA | 5 | 5 | — | 5 | 5 | — |
| IRG184 | 4.8 | 4.8 | 4.8 | 4.8 | 4.8 | 4.8 |
| BYK310 | 0.2 | 0.2 | 0.2 | 0.2 | 0.2 | 0.2 |

TABLE 2-continued

| Components | Resin 1 | Resin 2 | Resin 3 | Resin 4 | Resin 5 | Resin 6 |
| --- | --- | --- | --- | --- | --- | --- |
| Antimicrobial Monomer/Polymer | Example 1 5 | Example 5 20 | Example 12 25 | Example 15 25 | Example 20 25 | Example 23 25 |

(1) Coating Treatment

The above resins 1 to 6 were coated to a 10-um thickness (the coating thickness in a cured state) onto polycarbonate specimens using a #7 bar coater and then cured with UV light. With regard to the coated polycarbonate specimens, their physicochemical properties and functions were determined and the results are exhibited in Table 3 below.

TABLE 3

| Item | Resin 1 | Resin 2 | Resin 3 | Resin 4 | Resin 5 | Resin 6 |
| --- | --- | --- | --- | --- | --- | --- |
| Curability, 300 mJ/cm$^2$ | good | good | good | good | good | good |
| Adhesion Ability | 100/100 | 100/100 | 100/100 | 100/100 | 100/100 | 100/100 |
| Contamination Resistance | V.G | V.G | V.G | V.G | V.G | V.G |
| Anti-microbial Characteristics | grade 0 | grade 0 | grade 0 | grade 0 | grade 0 | grade 0 |
| Yellowing | pass | pass | pass | pass | pass | pass |

Curability: Determined by comparing the coating loss after 100 friction tests of surface methylethylketone and surface tacky properties after curing with the intensity of radiation of 300 mJ/cm2.
Adhesion Ability: Determined by the number of coating layers remained after marking 100-checker board scales on resins at 1 mm width and then taking them off with 3M scotch tape.
Contamination Resistance: After marking resins with an oily pen and then washing them with ethanol, it was designated as V.G. if there remains no surface mark, as G if traces remain, and as X if erasing was not possible.
Anti-microbial Characteristics: Determined according to ASTM G 21–22 against all kinds of bacterial strains
Anti-yellowing: Determined according to ASTM D1925.

From Table 3 above, it can be seen that the light-curable resins of the present invention have excellent curability and adhesion ability, very good contamination resistance, and high anti-microbial characteristics and anti-yellowing.

EXAMPLE 28

Manufacture I of Antimicrobial Coating Composition 12 g of butanol, 23 g of isopropyl alcohol, 25 g of butylcellosolve and 20 g of toluene were added to 1000 g of acryl resin solids (KA-961-50: Samhwa Paints Ind. Co., Ltd,), and stirred at a stirring speed of 650 rpm for 20 minutes. 351 g of titanium dioxide and 11 g of a wet dispersion agent (Trademark: Disperbyk-110) were added to the reactants, which were then evenly mixed by stirring them at the same speed for another 25 minutes, and thereafter dispersing using a sand mill. 8 g of the compound of Example 9 were diluted in 15 ml of the above mixture, to which 4.3 g of anti-foaming agent (Trademark: BYK-066) and 14 g of adhesion enhancer (Trademark: ADD-486) were added to manufacture the antimicrobial coating composition.

The antimicrobial characteristics of the above antimicrobial coating composition were determined, and it was proven that the antimicrobial coating composition of the present invention had bactericidal effects against various bacteria.

EXAMPLE 29

Manufacture II of Antimicrobial Coating Composition 15 g of butanol, 25 g of isopropyl alcohol, 25 g of butylcellosolve and 20 g of toluene were added to 1000 g of acryl resin solids (KA-961-50: Samhwa Paints Ind. Co., Ltd,), and stirred at a stirring speed of 650 rpm for 20 minutes. 345 g of titanium dioxide and 5 g of a wet dispersion agent (Trademark: Disperbyk-110) were added to the reactants, which were then evenly mixed by stirring them at the same speed for another 25 minutes, and thereafter dispersing using a sand mill. 10 g of the antimicrobial acrylic polymer of Example 20 were diluted in 20 ml of the above mixture, to which 3.3 g of an anti-foaming agent (Trademark: BYK-066) and 15 g of an adhesion enhancer (Trademark: ADD-486) were added to manufacture the coating. The antimicrobial characteristics of the above antimicrobial coating composition were determined and it was proven that the antimicrobial coating composition of the present invention had bactericidal effects against various bacteria.

EXAMPLE 30

Manufacture III of Antimicrobial Coating Composition

The coating was manufactured using the compound of Example 10 above according to the same method as in Example 28. The obtained antimicrobial coating composition exhibited bactericidal effects against various bacteria.

EXAMPLE 31

Manufacture IV of Antimicrobial Coating Composition

The coatings were manufactured using the compounds of Example 16 to 19 and 21 to 23 above, respectively, according to the same method as in Example 29. The produced antimicrobial coating compositions exhibited bactericidal effects against various bacteria.

EXPERIMENTAL EXAMPLE 1

Manufacture of Specimen and Antimicrobial Characteristics Determination Experiment The specimens were manufactured with the compositional ratios (units: wt. %) shown in Table 4 below, and their antimicrobial characteristics were determined.

That is, each of Examples 9, 10, 12, 13, 15, 19, 20, 22, and 23 was mixed with polyethylene, polypropylene, silicon resin, ABS, PS, acryl resin, natural rubber, or "HYBRAR" of Japanese Kuraray Co., LTD. and extruded or injected, and then blown to manufacture the specimens.

TABLE 4

| Component | Specimen 1 | Specimen 2 | Specimen 3 | Specimen 4 | Specimen 5 | Specimen 6 | Specimen 7 | Specimen 8 | Specimen 9 |
|---|---|---|---|---|---|---|---|---|---|
| PE | 95 | 2 | 30 | — | — | — | — | — | — |
| PP | 2 | 90 | 30 | — | — | — | — | — | — |
| HDPE | — | 2 | 30 | 2 | — | — | — | — | — |
| LDPE | — | 1 | — | 25 | — | — | — | — | — |
| LLDPE | — | — | 5 | 60 | 99 | — | — | — | — |
| Silicon | — | — | — | 10 | — | 99 | — | — | — |
| ABS | — | — | — | — | — | — | 99 | — | — |
| PC | — | — | — | — | — | — | — | 99 | — |
| PS | — | — | — | — | — | — | — | — | 99 |
| Antimicrobial Compound | Ex. 9 3 | Ex. 10 5 | Ex. 12 5 | Ex. 13 3 | Ex. 15 1 | Ex. 19 1 | Ex. 20 1 | Ex. 22 1 | Ex. 23 1 |

The antimicrobial characteristics of the above specimens 1 to 9 were determined by ASTM G 22, which is the antimicrobial test method of the American Society for Testing and Materials, and the yellowing was determined according to ASTM D1925. The antimicrobial characters were tested against *E. coli* (KCTC 1682).

TABLE 5

| Exp. Ex. | specimen 1 | specimen 2 | specimen 3 | specimen 4 | specimen 5 | specimen 6–9 |
|---|---|---|---|---|---|---|
| Anti-microbial characteristics | grade 0 | grade 0 | grade 0 | grade 0 | grade 0 | grade 0 |
| Yellowing | pass | pass | pass | pass | pass | pass |

The above Table 5 exhibits the results of the antimicrobial characteristics and yellowing tests of specimens 1 to 9, all of which had antimicrobial characteristics and did not cause yellowing.

EXPERIMENTAL EXAMPLE 2

Antimicrobial Test

The antimicrobial test was conducted by strain reduction rate determination (shake flask method). As the samples, 0.1 g of each of the compounds of Examples 9, 13, 15, and 18 to 23 was used in the form of powder, and in the case of Examples 28 to 31, 2 ml of their stock solution was used. The buffer solutions used in the antibacterial test were those prepared by dissolving each of 28.39 g of NaHPO4 and 23.99 g of NaH2PO4 in 1000 ml of purified water, blending them in the volume of 72 ml and 28 ml respectively, adding 5 g of NaCl thereto, and then pouring purified water thereinto to adjust their total volume to 1000 ml. As the control, the same bacterial strains, to which no samples were added, were used. The samples were mixed with bacterial strain inocula (5.0×105), which were then incubated while agitating for 24 hours and then incubated on agar media. The reduction rate of strain number was determined by the following Equation 1.

(Reduction Rate %)={(A−B)/A}×100    [Equation 1]

A: Number of Bacteria in Control after 24 Hours
B: Number of Bacteria in Sample after 24 Hours

TABLE 6

| Sample | | Right After Inoculation | After 24 hours | Strain Reduction Rate (%) |
|---|---|---|---|---|
| *E. coli* (KCTC 1682) | Control | $4.81 \times 10^4$ | $2.0 \times 10^7$ | — |
| | Example 9 | not detected | not detected | 100 |
| | Example 13 | not detected | not detected | 100 |
| | Example 15 | $1.5 \times 10^4$ | 1.99 | 99.99 |
| | Example 18 | $3.4 \times 10^5$ | 1.38 | 99.99 |
| | Example 19 | $4.8 \times 10^5$ | $2.22 \times 10^2$ | 99.99 |
| | Example 20 | $5.37 \times 10^5$ | 1.7 | 99.99 |
| | Example 21 | $5.06 \times 10^5$ | $1.22 \times 10^2$ | 99.99 |
| | Example 22 | $5.55 \times 10^5$ | $1.64 \times 10^2$ | 99.99 |
| | Example 23 | $4.33 \times 10^5$ | $1.35 \times 10^2$ | 99.99 |
| | Example 28 | $4.37 \times 10^5$ | 1.92 | 99.99 |
| | Example 29 | $4.99 \times 10^5$ | $3.44 \times 10^2$ | 99.99 |
| | Example 30 | $2.53 \times 10^5$ | 1.18 | 99.99 |
| | Example 31 | $3.96 \times 10^5$ | $2.09 \times 10^2$ | 99.99 |
| *S. aureus* (KCTC 1621) | Control | $5.34 \times 10^4$ | $2.05 \times 10^7$ | — |
| | Example 9 | not detected | not detected | 100 |
| | Example 13 | not detected | not detected | 100 |
| | Example 15 | $4.71 \times 10^4$ | 1.28 | 99.99 |
| | Example 18 | $5.6 \times 10^4$ | 1.14 | 99.99 |
| | Example 19 | $5.55 \times 10^5$ | 2.38 | 99.99 |
| | Example 20 | $4.11 \times 10^5$ | 6.25 | 99.99 |
| | Example 21 | $5.88 \times 10^5$ | $1.38 \times 10^2$ | 99.99 |
| | Example 22 | $3.62 \times 10^4$ | $1.01 \times 10^2$ | 99.99 |
| | Example 23 | $2.99 \times 10^4$ | $1.11 \times 10^2$ | 99.99 |
| | Example 28 | $5.77 \times 10^6$ | 3.08 | 99.99 |
| | Example 29 | $5.96 \times 10^6$ | $1.34 \times 10^2$ | 99.99 |
| | Example 30 | $4.21 \times 10^6$ | 2.15 | 99.99 |
| | Example 31 | $4.33 \times 10^6$ | $1.01 \times 10^2$ | 99.99 |

In Table 6 above, "right after inoculation" refers to after 5 minutes from the time the bacterial strains were inoculated. The antimicrobial monomer, antimicrobial acrylic copolymers, and antimicrobial polymeric resins of the present invention exhibited excellent bactericidal ability against *E. coli* and *S. aureus*. In addition, they exhibited good antimicrobial activity against *B. subtilis* and *M. luteus*.

EXPERIMENTAL EXAMPLE 3

Light Stability Test of Antimicrobial Acrylic Copolymer

The antimicrobial monomers manufactured in Examples 9 and 10 and the antimicrobial acrylic copolymers manufactured in Examples 17 to 23 were used as samples. 3 g of each sample were respectively put in lucid glass test tubes, which were then placed under a direct ray of light. Also, according to the same method, the samples were collected in lucid glass test tubes which were then sealed with aluminum foil and installed in a place where indoor light was shut off. The changes in color were observed every two weeks for 3 months, and the results are shown in Table 7 below.

From Table 7 above, it can be seen that the antimicrobial monomers of Examples 9 and 10 were not discolored when installed in the place where light was shut off, and Examples 17 to 23 maintained stable color for three months, and thus their light stability was excellent.

EXPERIMENTAL EXAMPLE 4

Skin Stimulation (Sensitivity) Test and Heat Resistance Test

The antimicrobial acrylic copolymers manufactured in Examples 15, 20, and 22 were each added to polyethylene resin in an amount of 10% by weight, and master-batched. The produced master batch was added to polyethylene for film in an amount of 5% by weight, and blown to manufacture a film. The film was cut into patches of 5 cm wide×5 cm long, and 5 adult males and 5 adult females were subjected to a patch test with them for 24 hours. The results are shown in Table 8 below, and it can be seen that no abnormal symptoms were observed in any of the subjects of the test.

TABLE 7

| | | Initial | Two Weeks Later | Four Weeks Later | Six Weeks Later | Eight Weeks Later | Ten Weeks Later | Twelve Weeks Later |
|---|---|---|---|---|---|---|---|---|
| Direct Ray of Light | Example 9 | white | yellow | orange | light brown | light brown | brown | brown |
| | Example 10 | white | yellow | orange | light brown | light brown | brown | brown |
| Light Shut Off | Example 9 | white | white | white | white | white | white | white |
| | Example 10 | white | white | white | white | white | white | white |
| Direct Ray of Light | Example 17 | white | white | white | white | white | white | white |
| | Example 18 | white | white | white | white | white | white | white |
| | Example 19 | light yellow | light yellow | light yellow | light yellow | light yellow | light yellow | light yellow |
| | Example 20 | light yellow | light yellow | light yellow | light yellow | light yellow | light yellow | light yellow |
| | Example 21 | light yellow | light yellow | light yellow | light yellow | light yellow | light yellow | light yellow |
| | Example 22 | yellow | yellow | yellow | yellow | yellow | yellow | yellow |
| | Example 23 | yellow | yellow | yellow | yellow | yellow | yellow | yellow |
| Light Shut Off | Example 17 | white | white | white | white | white | white | white |
| | Example 18 | white | white | white | white | white | white | white |
| | Example 19 | light yellow | light yellow | light yellow | light yellow | light yellow | light yellow | light yellow |
| | Example 20 | light yellow | light yellow | light yellow | light yellow | light yellow | light yellow | light yellow |
| | Example 21 | light yellow | light yellow | light yellow | light yellow | light yellow | light yellow | light yellow |
| | Example 22 | yellow | yellow | yellow | yellow | yellow | yellow | yellow |
| | Example 23 | yellow | yellow | yellow | yellow | yellow | yellow | yellow |

TABLE 8

|  | Gender | 1 Hour Later | 3 Hours Later | 6 Hours Later | 12 Hours Later | 24 Hours Later |
|---|---|---|---|---|---|---|
| Example 15 | Male | x | x | x | x | x |
|  | Female | x | x | x | x | x |
| Example 20 | Male | x | x | x | x | x |
|  | Female | x | x | x | x | x |
| Example 22 | Male | x | x | x | x | x |
|  | Female | x | x | x | x | x | x: No Skin Stimulation
o: Skin Stimulation (Eruption, Red Spot, Tickling, Etc.)

Also, to investigate heat stability during the molding process, an antimicrobial test was conducted with regard to each film, and the results are shown in Table 9.

TABLE 9

| Sample |  | Right After Innoculation[5] | 24 Hours Later | Microbe Reduction Rate(%) |
|---|---|---|---|---|
| E. coli (KCTC 1682) | Control | $5.44 \times 10^5$ | $2.38 \times 10^7$ | — |
|  | Polyethylene 1[2] | $6.66 \times 10^5$ | $1.11 \times 10^2$ | 99.99 |
|  | Polyethylene 2[3] | $7.21 \times 10^5$ | $1.32 \times 10^2$ | 99.99 |
|  | Polyethylene 3[4] | $5.18 \times 10^5$ | $2.16 \times 10^2$ | 99.99 |
| S. aureus (KCTC 1621) | Polyethylene 1[2] | $7.77 \times 10^5$ | $1.88 \times 10^2$ | 99.99 |
|  | Polyethylene 2[3] | $8.01 \times 10^5$ | $2.11 \times 10^2$ | 99.99 |
|  | Polyethylene 3[4] | $6.55 \times 10^5$ | $1.99 \times 10^2$ | 99.99 |
| B. subtilis (KCTC 1021) | Polyethylene 1[2] | $7.02 \times 10^5$ | $1.98 \times 10^2$ | 99.99 |
|  | Polyethylene 2[3] | $8.33 \times 10^5$ | $2.13 \times 10^2$ | 99.99 |
|  | Polyethylene 3[4] | $7.99 \times 10^5$ | $2.71 \times 10^2$ | 99.99 |
| M. luteus (KCTC 1071) | Polyethylene 1[2] | $7.94 \times 10^5$ | $2.24 \times 10^2$ | 99.99 |
|  | Polyethylene 2[3] | $8.55 \times 10^5$ | $2.75 \times 10^2$ | 99.99 |
|  | Polyethylene 3[4] | $8.68 \times 10^5$ | $1.99 \times 10^2$ | 99.99 |

Notes)
The amount of strains was $5.0 \times 10^5$ when initially inoculated.
[1]Strain reduction rate determination
[2]Polyethylene film manufactured by Example 15
[3]Polyethylene film manufactured by Example 20
[4]Polyethylene film manufactured by Example 22
[5]Number of bacteria after 5 minutes from the time the strains were inoculated As shown in Table 9, it can be seen that the polyethylene films exhibited excellent antimicrobial effects even after the molding process, and no sudden reduction in antimicrobial abilities due to heat decomposition of antimicrobial substances was observed during the molding process into products.

EXPERIMENTAL EXAMPLE 5

Elution Test 4 g of each of the antimicrobial acrylic copolymers manufactured in Examples 20 and 22 above were added to 20 ml of 0.9% NaCl aqueous solution, and after 24 hours at 70° C., they were cooled to room temperature and then filtered to prepare elution test solutions. The antimicrobial effects of samples before and after tests and the elution test solution were determined and compared, and they are exhibited in Table 10 below. The solid samples were used in an amount of 20 µg, respectively, in the form of powder, and elution solutions were determined by dripping 20 µl of them on a paper disc.

TABLE 10

|  |  | E. coli (KCTC 1682) | S. aureus (KCTC 1621) | B. subtilis (KCTC 1021) | M. luteus (KCTC 1071) |
|---|---|---|---|---|---|
| Application 1[2] | Before Elution | 3.0 mm ± 0.5 mm | 1.0 mm ± 0.5 mm | 1.5 mm ± 0.5 mm | 2.5 mm ± 0.5 mm |
|  | After Elution | 3.0 mm ± 0.5 mm | 1.0 mm ± 0.5 mm | 1.5 mm ± 0.5 mm | 2.5 mm ± 0.5 mm |
|  | Elution Test Solution | 0 mm | 0 mm | 0 mm | 0 mm |
| Application 2[3] | Before Elution | 2.5 ± 1 mm | 0.5 ± 1 mm | 1.0 mm ± 0.5 mm | 1.0 mm ± 0.5 mm |
|  | After Elution | 2.5 ± 1 mm | 0.5 ± 1 mm | 1.0 mm ± 0.5 mm | 1.0 mm ± 0.5 mm |
|  | Elution Test Solution | 0 mm | 0 mm | 0 mm | 0 mm |

[2]Antimicrobial acrylic copolymer of Example 20
[3]Antimicrobial acrylic copolymer of Example 22

From Table 10 above, it can be seen that all the samples both before and after the elution test formed an inhibition zone having the same size, but in the elution test solutions, no inhibition zone was formed.

EXPERIMENTAL EXAMPLE 6

Oral Toxicity (Acute Toxicity) Test of Antimicrobial Acrylic Copolymer

An oral toxicity test was conducted using the elution solution of Example 20 above.

The test procedures followed No. 1999-61 of the Korea Food & Drug Administration Notification. The test animals were Balb/C mice of Samtaco, Co., and 5 each of five weeks-old male and female mice were used. An oral administration route was used, the number of administrations was once, and a compulsory oral administration method using a sonde was employed. On the day the administration was carried out, general conditions were observed every hour for 12 hours, and from the day after administration to 14 days, changes in general conditions, addiction symptoms, motion ability, appearance, and presence of dead animals were observed once a day.

6-1. $LD_{50}$

As a result of the administration of 20 ml/kg B.W., which is the established maximum administrable amount, no dead animals were observed. Therefore, it was impossible to calculate a rough lethal dose.

6-2. Death Rate

During the whole period of the test, no deaths of the animals tested were observed.

6-3. Clinic Symptom

Throughout the whole period of the test, no specific clinical symptoms appeared.

According to the above results, it can be seen that the antimicrobial acrylic copolymers were comparatively stable in respect of oral toxicity.

EXAMPLE 32

Fabrication of Antimicrobial Master Batch for Medical Purpose and Antimicrobial Test The antimicrobial monomers and antimicrobial polymeric compounds manufactured in Examples 9, 10, 15, and 22 above, and a dispersion agent LLDPE resin and an antioxidant agent, which are commercially ordinary, were each charged into a high-speed combining machine. They were then combined by stirring them at a high speed for 30 minutes, followed by injection-molding them in an injection molding machine at a molding temperature of 170~190° C., to prepare the antimicrobial master batch in the form of a pellet. Also, according to the same method, they were applied to HDPE and PP to thereby prepare the antimicrobial master batches, respectively. The ratios of each composition are as shown Table 11 below. The antimicrobial test was performed by strain reduction rate determination (Shake flask method), and the results are shown in Table 12.

TABLE 12

Antimicrobial Test Results of Antimicrobial Master Batch for Medical Purpose

|  | E. coli (KCTC 1682) | S. aureus (KCTC 1621) | S. typhimurium (KCTC 1925) | P. aeruginosa (KCTC 2004) |
|---|---|---|---|---|
| Composition V | 99.99 | 99.99 | 99.99 | 99.99 |
| Composition VI | 99.99 | 99.99 | 99.99 | 99.99 |
| Composition VII | 99.99 | 99.99 | 99.99 | 99.99 |
| Composition VIII | 99.99 | 99.99 | 99.99 | 99.99 |

EXAMPLE 33

Fabrication of Antimicrobial Catheter for Medical Purpose

The antimicrobial polymeric compounds produced by Examples 15 and 22 were each added to medical grade silicon resin, with which catalysts, etc. were roll-combined with the compositional ratios shown in Table 13 below for 30~60 minutes and then processed by an injection molding machine to thereby fabricate an antimicrobial Foley catheter in the form of a tube. The molding process temperature was 450° C.~600° C.×10 seconds, and the product was cured for 2 hours by being maintained in a dryer at 200° C. The antimicrobial effect was tested by strain reduction rate determination (Shake flask method), and the results are summarized in Table 14.

TABLE 11

Compositional Ratios of Antimicrobial Master Batch for Medical Purpose

|  | Antimicrobial Substance | LLDPE[1] | HDPE[2] | PP[3] | Dispersion Agent/ Lubricant[4] | Anti-Oxidant Agent[5] | Dispersion Agent[6] | Total (wt. %) |
|---|---|---|---|---|---|---|---|---|
| Composition V | Example 9 (5%) | 82.9 | — | — | 2 | 0.1 | 10 | 100 |
| Composition VI | Example 10 (5%) | — | 82.9 | — | 2 | 0.1 | 10 | 100 |
| Composition VII | Example 15 (5%) | — | — | 83.4 | 1.5 | 0.1 | 10 | 100 |
| Composition VIII | Example 22 (5%) | 82.9 | — | — | 2 | 0.1 | 10 | 100 |

Notes)
[1]SK (Co.) Trademark CA 110;
[2]SK (Co.) Trademark JH 910;
[3]Trademark H360F;
[4]N,N'-ethylene bis steamide (E.B.S);
[5]n-octadecyl-3(3'-5'-di-t-butyl-4-hydroxyphenyl) propionate;
[6]Polyethylene Wax

TABLE 13

Compositional Ratios of Antimicrobial Silicon Foley Catheter

|  | Peroxide Catalyst | Pt Catalyst | Antimicrobial Substance Example 15 | Antimicrobial Substance Example 22 | Silicon Resin | Total (wt. %) |
|---|---|---|---|---|---|---|
| Composition I | — | 0.2 | 2.0 | — | 97.8 | 100 |
| Composition II | 0.2 | — | — | 2.0 | 97.8 | 100 |

TABLE 14

Antimicrobial Test Results of Antimicrobial Silicon Foley Catheter

|  | S. aureus (AATC 1621) | E. coli (AATC 1682) | P. aeruginosa (AATC 2004) |
|---|---|---|---|
| Composition I | 99.99 | 99.99 | 99.99 |
| Composition II | 99.99 | 99.99 | 99.99 |

EXAMPLE 34

Fabrication of Antimicrobial Polyurethane Artificial Legs for Medical Purpose

Medical grade polyurethane resins and the antimicrobial polymeric compounds obtained from Examples 15 and 22 were roll-combined for 2 hours with the compositional ratios shown in Table 15 below, then injected into a mold and vulcanized for 1 hour by being maintained at 160° C., and then cooled to room temperature to thereby fabricate antimicrobial polyurethane artificial legs. The antimicrobial performance was tested by the Shake flask method (Strain Reduction Rate Determination), and the determination results are shown in Table 16 below.

TABLE 15

Compositional Ratios of Antimicrobial Polyurethane Artificial Legs

| Category | Antimicrobial Material Example 15 | Antimicrobial Material Example 22 | Polyurethane Resin | Total (wt. %) |
|---|---|---|---|---|
| Composition III | 1.0 | — | 99.0 | 100 |
| Composition IV | — | 1.0 | 99.0 | 100 |

TABLE 16

Antimicrobial Test Results of Antimicrobial Polyurethane Artificial Legs

| Strains Composition | S. aureus (AATC 1621) | E. coli (AATC 1682) | P. aeruginosa (AATC 2004) |
|---|---|---|---|
| Composition III | 99.99 | 99.99 | 99.99 |
| Composition IV | 99.99 | 99.99 | 99.99 |

As mentioned above, the antimicrobial monomers and antimicrobial polymeric compounds using them of the present invention have durable antimicrobial activity and high heat resistance, they do not give rise to toxicity when added to petrochemical materials such as conventional polymeric resins by not eluting the antimicrobial compounds, and they do not have an effect on the properties of molded products. Accordingly, the antimicrobial monomers of the present invention and the antimicrobial polymeric compounds using them can be easily and simply applied to industrial supplies such as various coatings, fibers, architectural materials, rubbers, medical supplies including medical devices for living bodies, and consumer supplies.

What is claimed is:

1. An antimicrobial acrylic copolymer having an average molecular weight of 10,000~1,000,000, represented by the following formula 10:

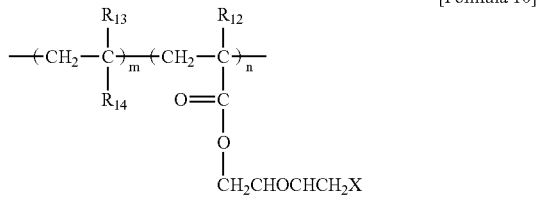

[Formula 10]

wherein $R_{12}$ and $R_{13}$ are each independently or simultaneously hydrogen or a methyl group;

$R_{14}$ is a $C_1$~$C_{18}$ alkyl group comprising one or more selected from the group consisting of ester, carbonyl, amide, amine, cycloalkyl, ether, hydroxy, carboxylic acid, $C_2$~$C_{10}$ hetero ring containing N or O, sulfonyl, silane, lactone, and aldehyde groups;

m and n are each an integer greater than zero satisfying said molecular weight; and X is a compound of the following formula 2a:

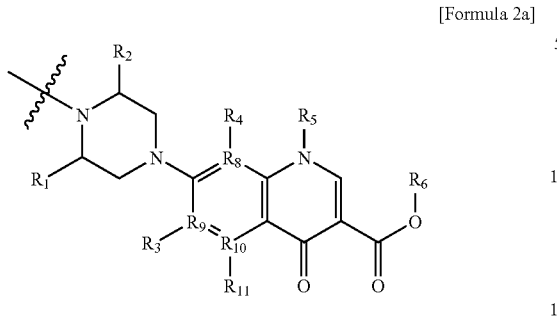

[Formula 2a]

wherein $R_1$ and $R_2$ are each independently or simultaneously hydrogen, a halogen atom, an amine, or a $C_1$~$C_{20}$ alkyl group; $R_3$ and $R_4$ are each independently or simultaneously hydrogen, a hydroxy group, a $C_1$~$C_{20}$ alkoxide, a halogen atom, or a $C_1$~$C_{20}$ alkyl group; $R_5$ is hydrogen, a $C_1$~$C_{20}$ alkyl, a cyclopropyl, or an aromatic $C_1$~$C_{20}$ hydrocarbon; $R_6$ is hydrogen, sodium, potassium, or a $C_1$~$C_{150}$ alkyl group that comprises or does not comprise a polymerizable functional group; $R_8$, $R_9$, and $R_{10}$ are each independently or simultaneously carbon or nitrogen; and $R_{11}$ is hydrogen, an amine (1°, 2°, 3°), a halogen atom, or a $C_1$~$C_{20}$ alkyl group.

2. A method of manufacturing the antimicrobial acrylic copolymer of formula 10 of claim 1, comprising the step of radically polymerizing a compound of the following formula 11:

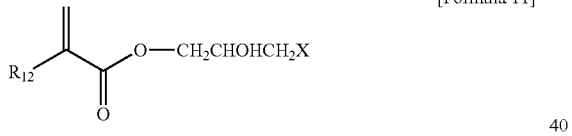

[Formula 11]

wherein $R_{12}$ is hydrogen or a methyl group, and wherein X is a compound of the following formula 2a

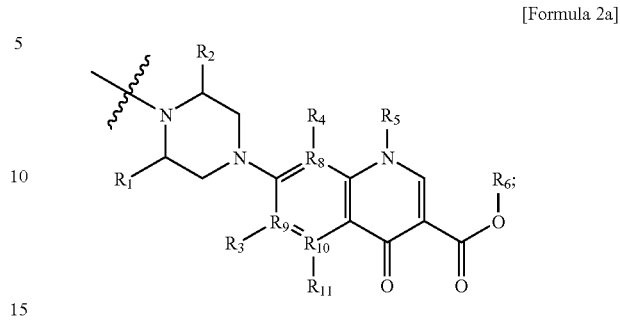

[Formula 2a]

with a compound of the following formula 12:

[Formula 12]

wherein $R_{13}$ is hydrogen or a methyl group, and $R_{14}$ is a $C_1$~$C_{18}$ alkyl group comprising one or more selected from the group consisting of ester, carbonyl, amide, amine, cycloalkyl, ether, hydroxy, carboxylic acid, $C_2$~$C_{10}$ hetero ring containing N or O, sulfonyl, silane, lactone, and aldehyde groups.

3. The method of the antimicrobial acrylic copolymer of claim 2, characterized in that said compound of formula 12 is an acrylic monomer consisting of a hydrocarbon main chain attributed to a vinyl alcohol, acrylonitrile, butadiene, acrylic acid, styrene, acrylimide, methylmethacrylic acid, methacrylic acid, vinylchloride, vinylfluoride, or vinylacetateacrylic acid as a main chain.

* * * * *